United States Patent [19]

Mitchell et al.

[11] Patent Number: 4,568,341
[45] Date of Patent: Feb. 4, 1986

[54] ABSORBENT PADS, INCONTINENCE CARE PRODUCTS AND METHODS OF PRODUCTION

[75] Inventors: James G. Mitchell; Winalee G. Mitchell, both c/o of Principle Business Enterprises, Pine Lake Industrial Park, Dunbridge, Ohio 43414; Robert E. Strauss; Charles J. Strader, both of Perrysburg, Ohio; William C. Bollinger, Troy; Jerry L. Bell, Rochester, both of Mich.

[73] Assignees: James G. Mitchell; Winalee G. Mitchell, both of Perrysburg, Ohio

[21] Appl. No.: 474,253

[22] Filed: Mar. 10, 1983

[30] Foreign Application Priority Data

Mar. 10, 1982 [WO] PCT Int'l Appl. .................. PCT/US82/00312

[51] Int. Cl.$^4$ .............................................. A61F 13/20
[52] U.S. Cl. .................................... 604/368; 604/378; 604/396
[58] Field of Search ............... 604/378, 368, 383, 385, 604/393, 396, 364, 367

[56] References Cited

U.S. PATENT DOCUMENTS

| | | |
|---|---|---|
| 810,120 | 1/1906 | Green . |
| 1,843,037 | 1/1932 | Mathey . |
| 2,684,240 | 7/1954 | Lindsey ................... 271/2.3 |
| 3,046,986 | 7/1962 | Harwood ................ 128/290 |
| 3,178,494 | 4/1965 | Tisdale ........................ 264/90 |
| 3,286,435 | 11/1966 | Weinberger ............... 53/117 |
| 3,289,254 | 12/1966 | Joa ............................. 19/145 |
| 3,395,708 | 8/1968 | Hervey et al. ............ 128/284 |
| 3,472,724 | 10/1969 | Casey ........................ 156/521 |
| 3,491,759 | 1/1970 | Samuel ...................... 128/290 |
| 3,525,337 | 8/1970 | Simons et al. ............ 128/290 |
| 3,545,442 | 12/1970 | Wicker et al. ............ 604/383 |
| 3,610,244 | 10/1971 | Jones, Sr. ................. 128/287 |
| 3,620,894 | 11/1971 | Oates ........................ 604/383 |
| 3,653,382 | 4/1972 | Easley et al. ............. 128/284 |
| 3,666,611 | 5/1972 | Joa ............................ 161/147 |
| 3,676,263 | 7/1972 | Tisdale ..................... 156/462 |
| 3,773,587 | 11/1973 | Flewwelling ............. 156/201 |

(List continued on next page.)

FOREIGN PATENT DOCUMENTS

| | | |
|---|---|---|
| 752366 | 6/1970 | Belgium . |
| 317413 | 12/1973 | Belgium . |
| 2554640 | 6/1976 | Fed. Rep. of Germany . |
| 2559606 | 12/1980 | Fed. Rep. of Germany . |
| 1316833 | 5/1973 | United Kingdom . |
| 1500559 | 2/1978 | United Kingdom . |
| 1515768 | 6/1978 | United Kingdom . |
| 2017509 | 5/1979 | United Kingdom . |

OTHER PUBLICATIONS

Ahlgren et al., "The Billerud Fluff Concept and Cekosorb Super-Absorbent" Sep. 16-18, 1981 Section II, pp. 1-19.
Dow Water Absorbent Laminate (Brochure) 1979.

Primary Examiner—C. Fred Rosenbaum
Assistant Examiner—Sherri Vinyard
Attorney, Agent, or Firm—John C. Purdue

[57] ABSTRACT

The invention addresses problems with liquid absorbent pads having at least about 50% of their absorption capacity represented by water absorbent (including water-swellable) material capable of absorbing at least about 5 times its own dry weight of aqueous liquid. By openings of specified area, present in undulating layer(s) of such absorbent material in specified numbers and total area per unit area of said layer(s), and/or through forming such openings as hinges and displaced flap members for locking the layers of a moving composite together for bending into said undulating configuration, and/or through use of sheath members of material which substantially retain their structural integrity in contact with aqueous liquids, and have open or openable portion(s), pads are formed with both high absorption rate and capacity and/or ready disposability and/or rapid production characteristics, ideally suited for urinary incontinence care and other uses.

22 Claims, 43 Drawing Figures

U.S. PATENT DOCUMENTS

| | | | |
|---|---|---|---|
| 3,783,872 | 1/1974 | King | 128/290 R |
| 3,805,790 | 4/1974 | Kaczmarzyk et al. | 128/290 |
| 3,809,089 | 5/1974 | Hedstrom et al. | 128/287 |
| 3,865,112 | 2/1975 | Roeder | 128/290 |
| 3,886,941 | 6/1975 | Duane et al. | 128/247 |
| 3,888,256 | 6/1975 | Studinger | 128/296 |
| 3,890,974 | 6/1975 | Kozak | 128/287 |
| 3,903,889 | 9/1975 | Torr | 128/287 |
| 3,927,673 | 12/1975 | Taylor | 128/132 |
| 3,928,105 | 12/1975 | Holden | 156/200 |
| 3,987,792 | 10/1976 | Hernandez et al. | 128/284 |
| 4,044,769 | 8/1977 | Papajohn | 128/284 |
| 4,055,180 | 10/1977 | Karami | 128/287 |
| 4,055,184 | 10/1977 | Karami | 128/284 |
| 4,069,821 | 1/1978 | Fitzgerald et al. | 128/290 |
| 4,093,765 | 6/1978 | Schmidt | 428/134 |
| 4,096,312 | 6/1978 | Holst et al. | 428/297 |
| 4,105,033 | 8/1978 | Chatterjee et al. | 128/285 |
| 4,117,184 | 9/1978 | Erickson et al. | 428/224 |
| 4,155,893 | 5/1979 | Fujimoto et al. | 260/29.6 |
| 4,172,066 | 10/1979 | Zweigle et al. | 260/29.6 |
| 4,173,046 | 11/1979 | Gallagher | 5/484 |
| 4,176,667 | 12/1979 | Herring | 128/287 |
| 4,252,391 | 2/1981 | Rosenberg | 156/203 |
| 4,282,874 | 8/1981 | Mesek | 604/383 |
| 4,293,609 | 10/1981 | Erickson | 428/246 |
| 4,296,234 | 10/1981 | Mindt | 536/47 |
| 4,297,410 | 10/1981 | Tsuchiya et al. | 428/283 |
| 4,306,559 | 12/1981 | Nishizawa et al. | 128/287 |
| 4,317,449 | 3/1982 | Nowakowski | 128/287 |
| 4,333,464 | 6/1982 | Nakano | 128/290 |

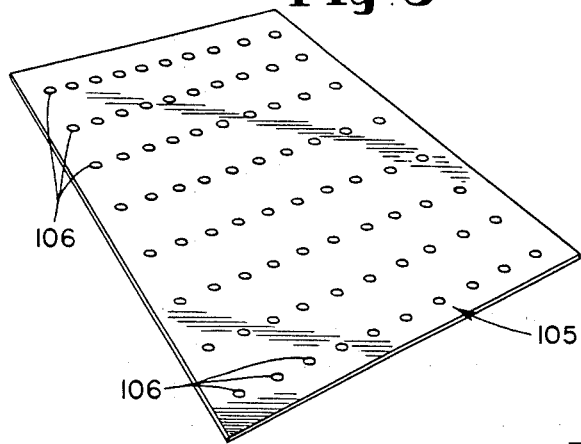
Fig. 5
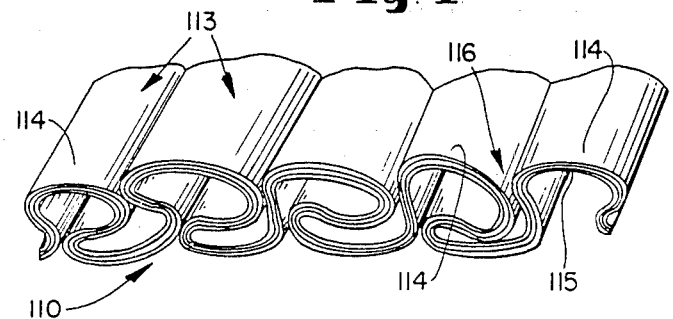
Fig. 7
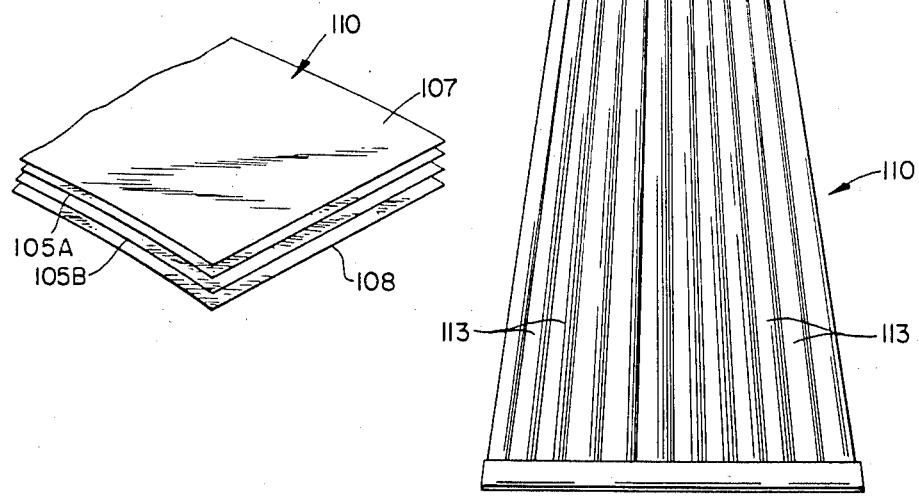
Fig. 6
Fig. 8

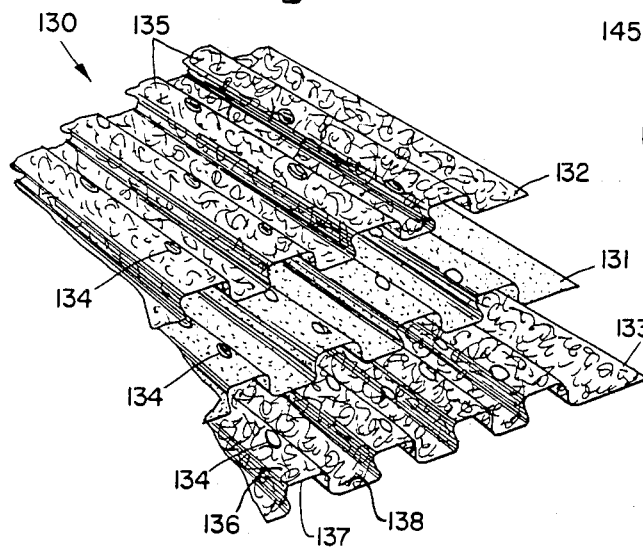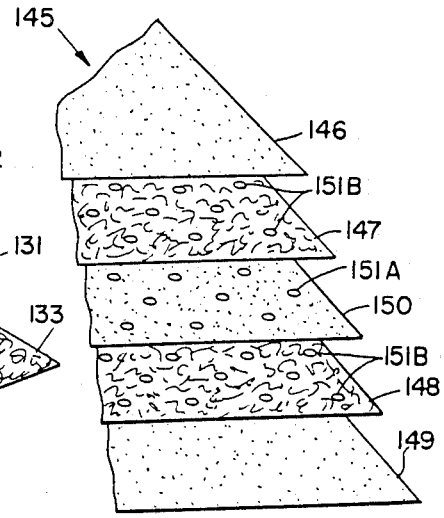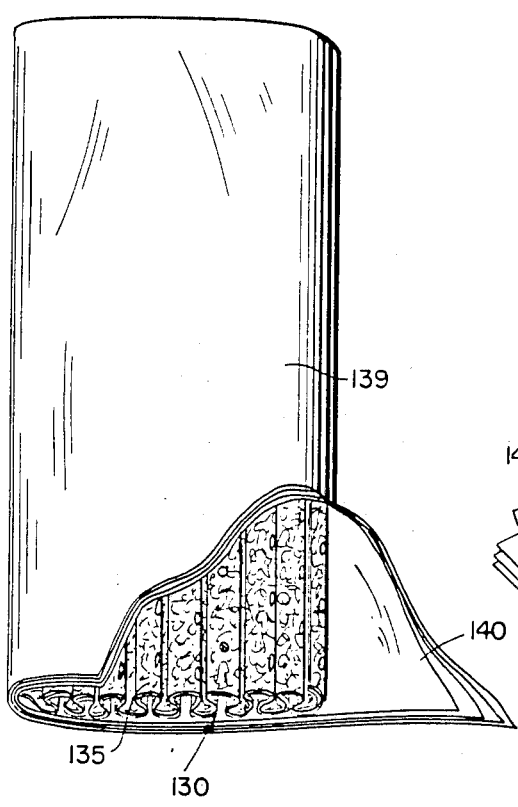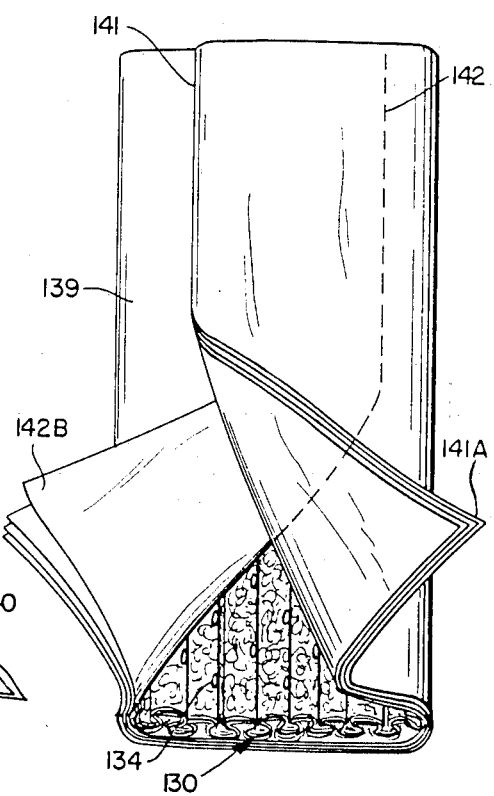

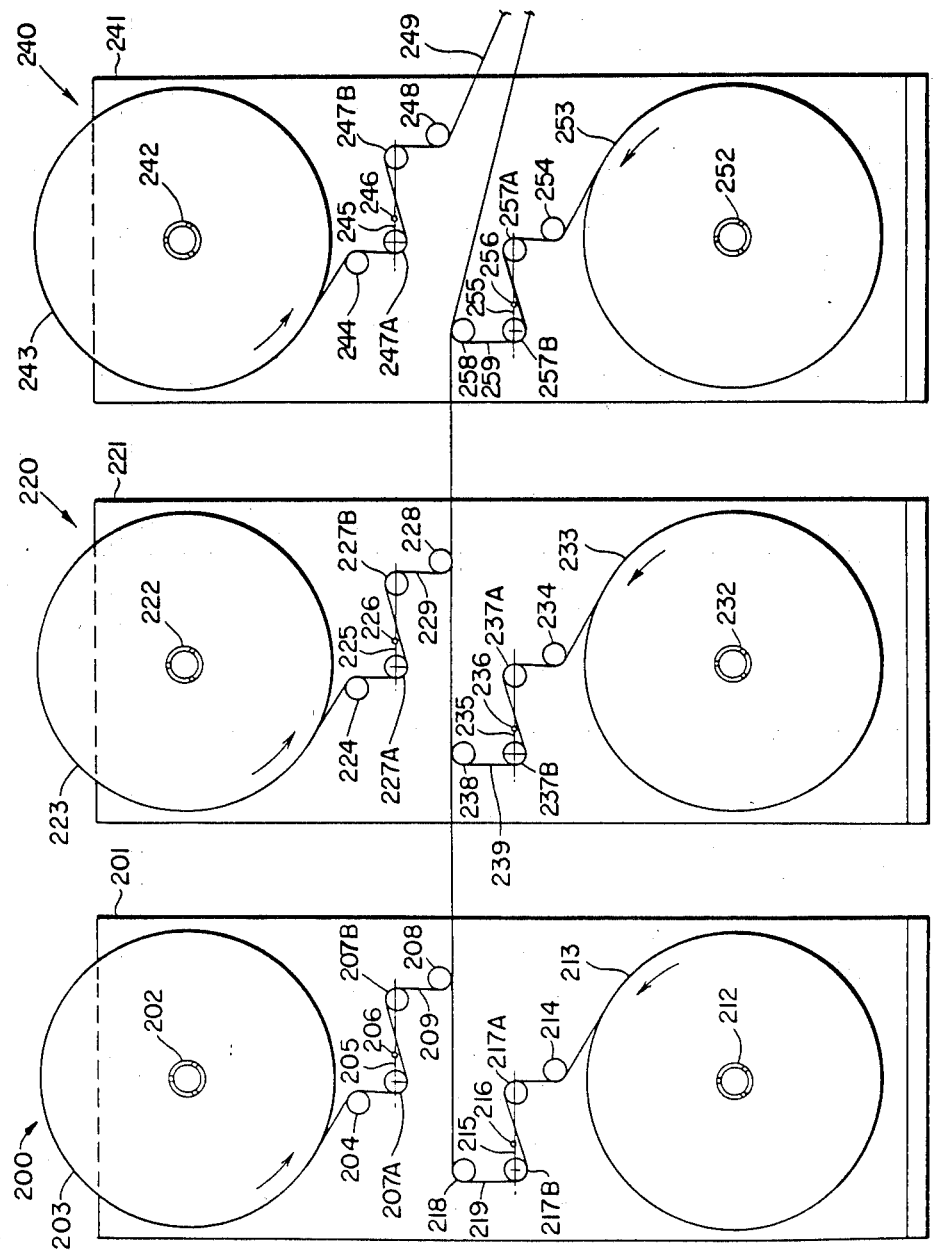

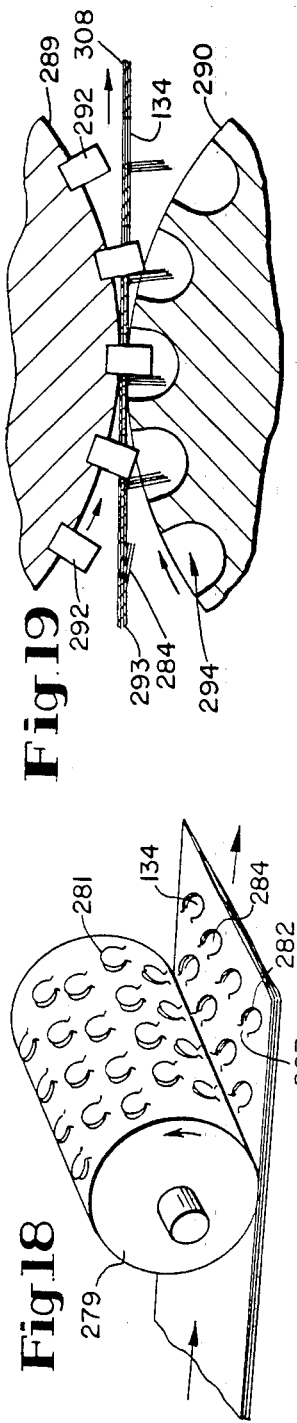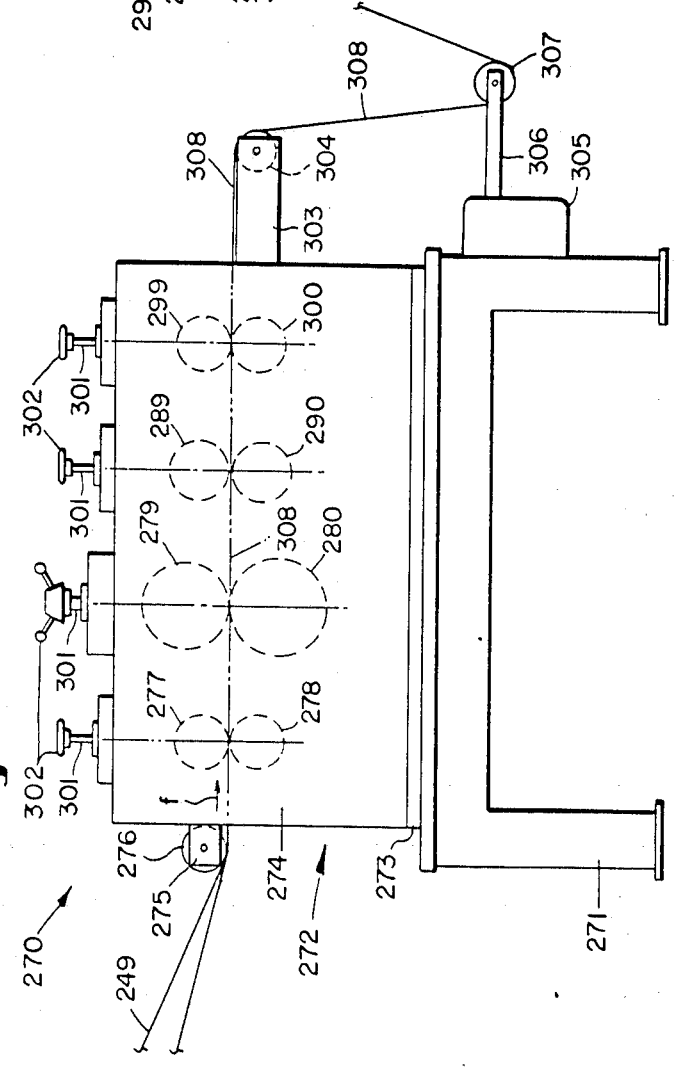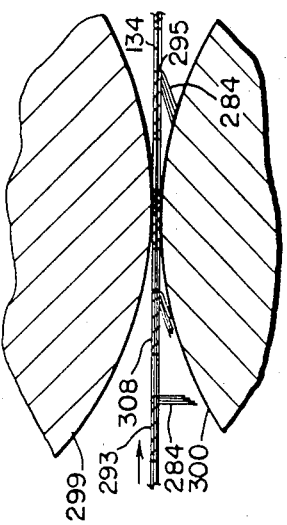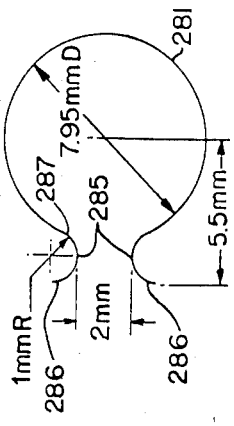

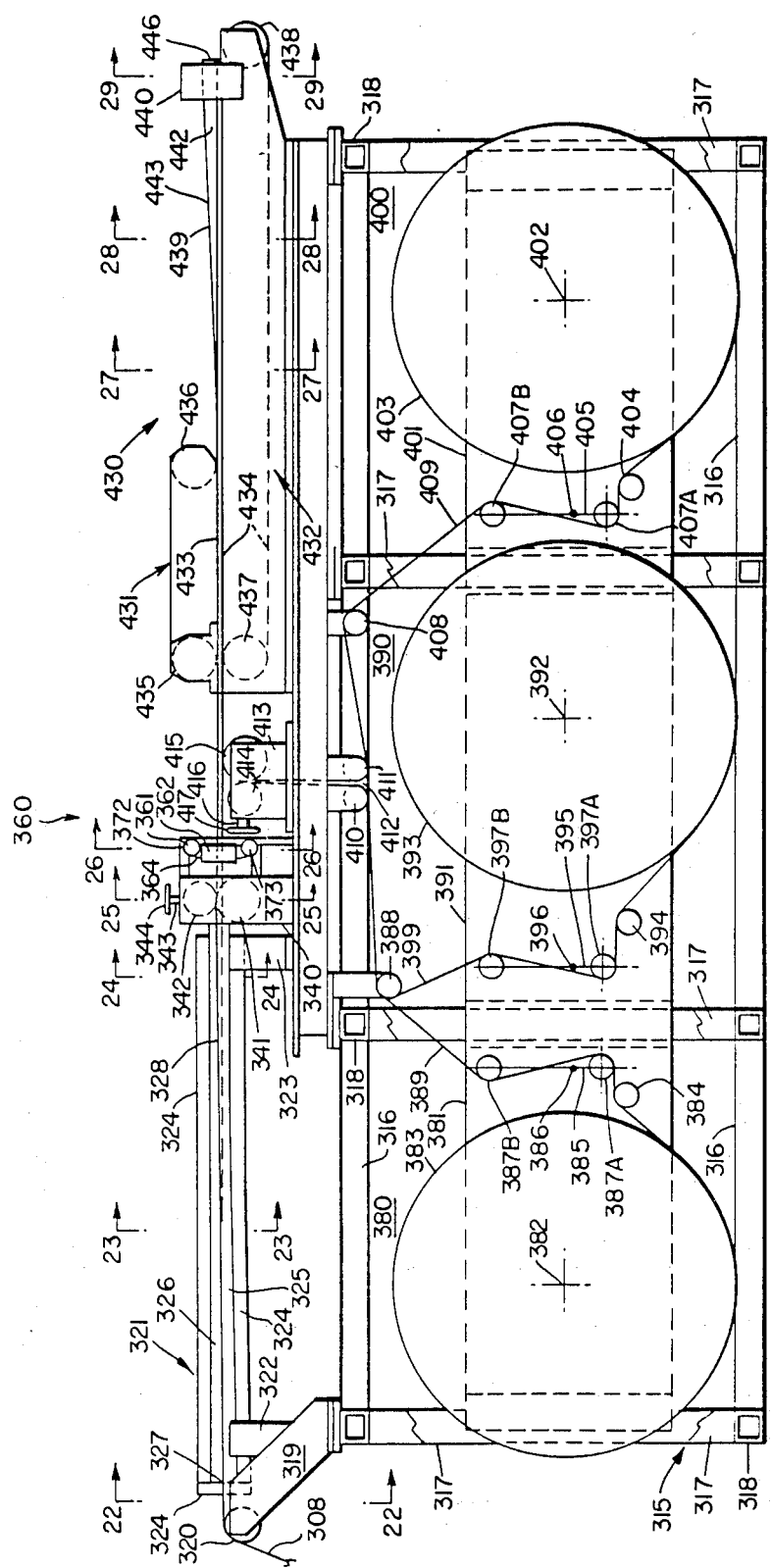

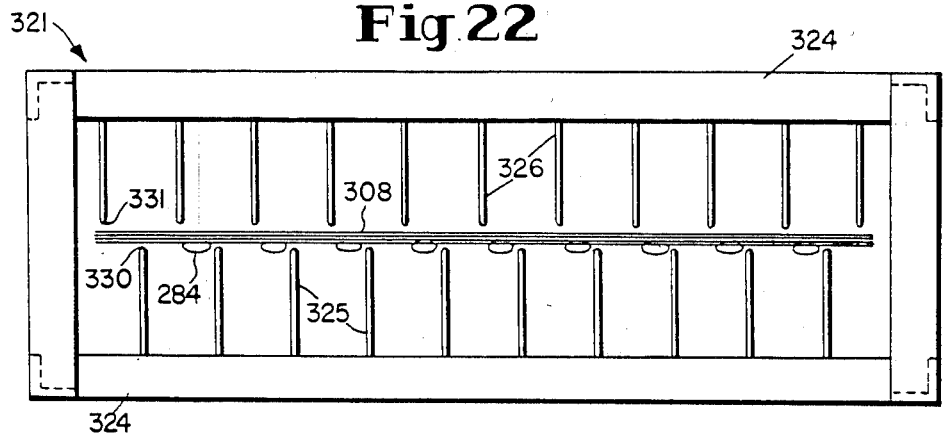
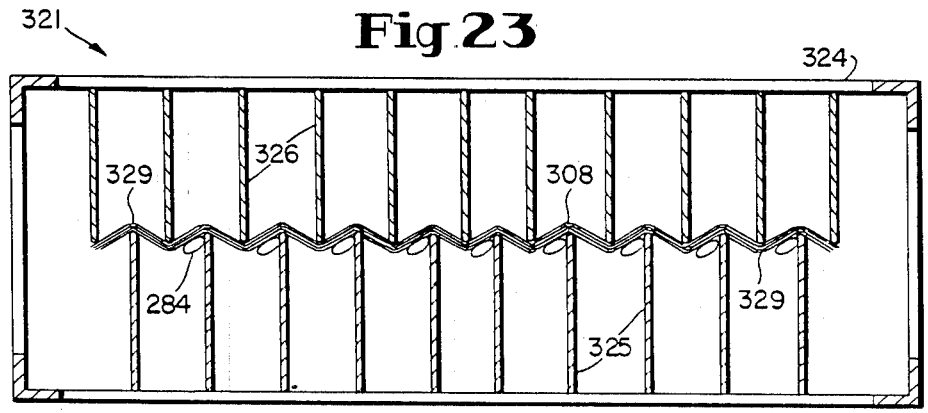
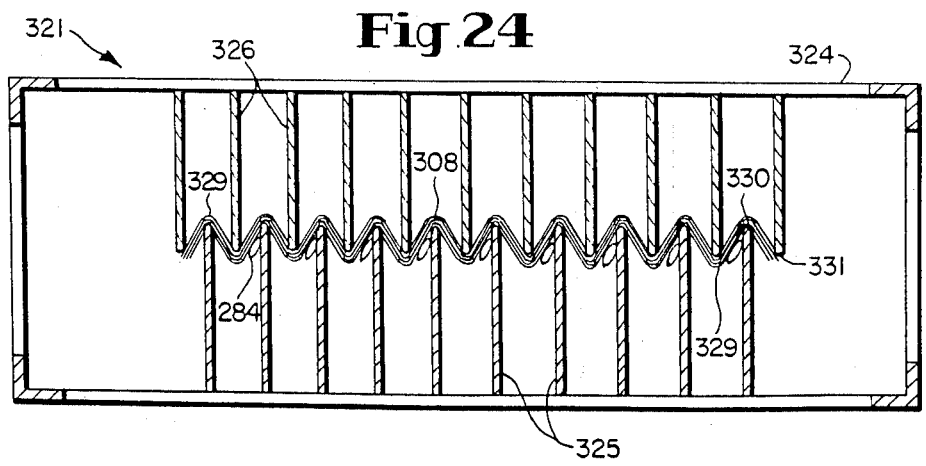

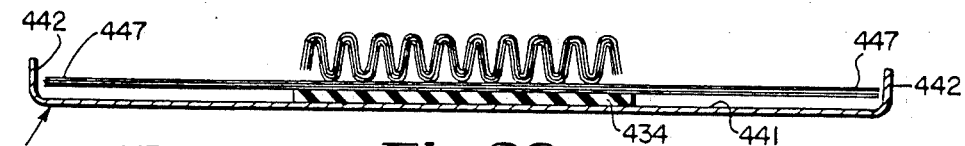
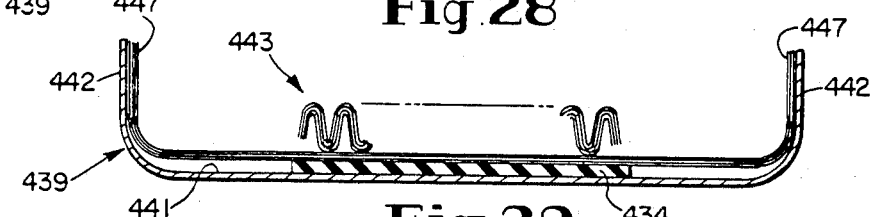
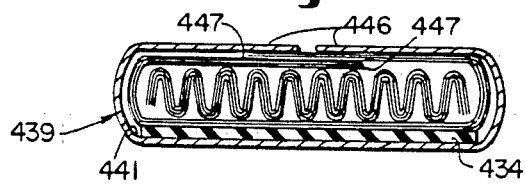
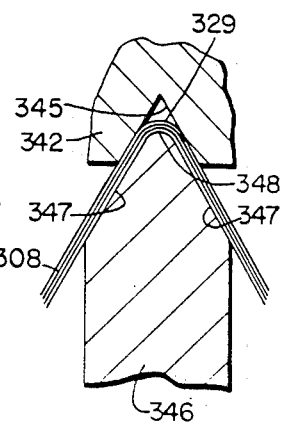
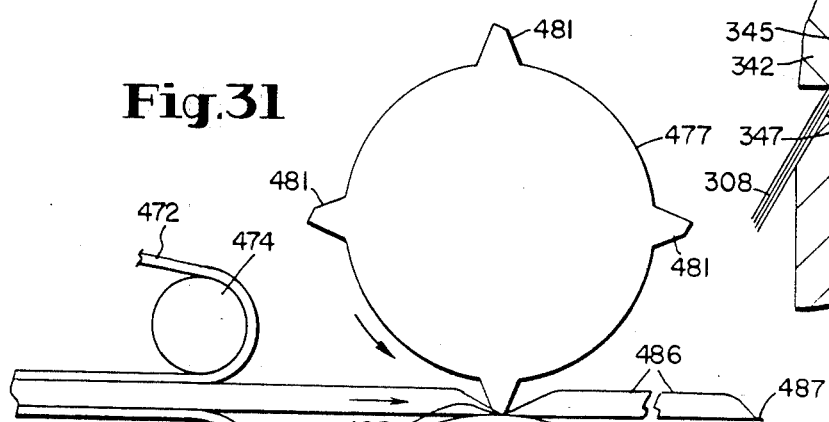
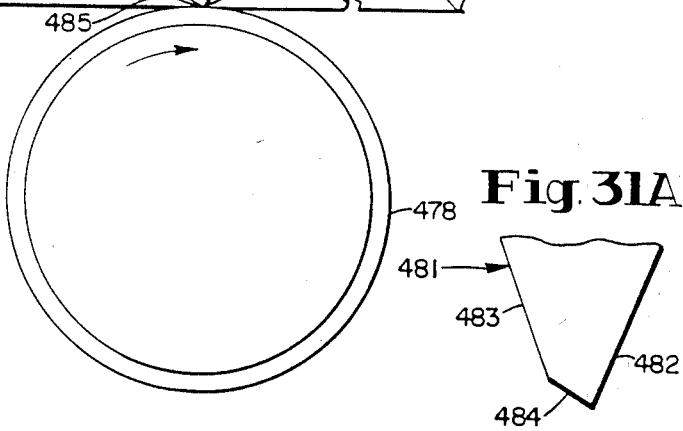

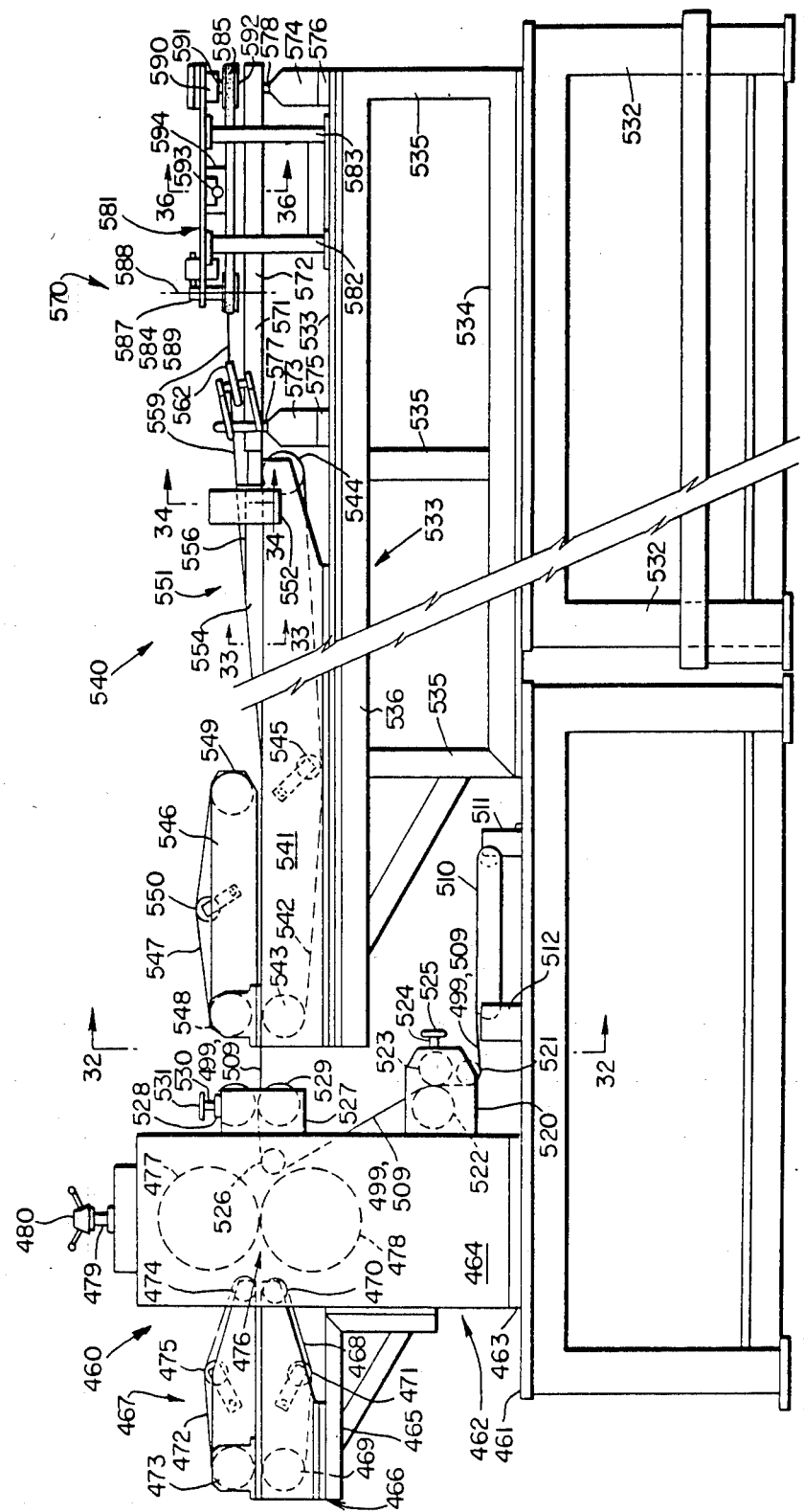

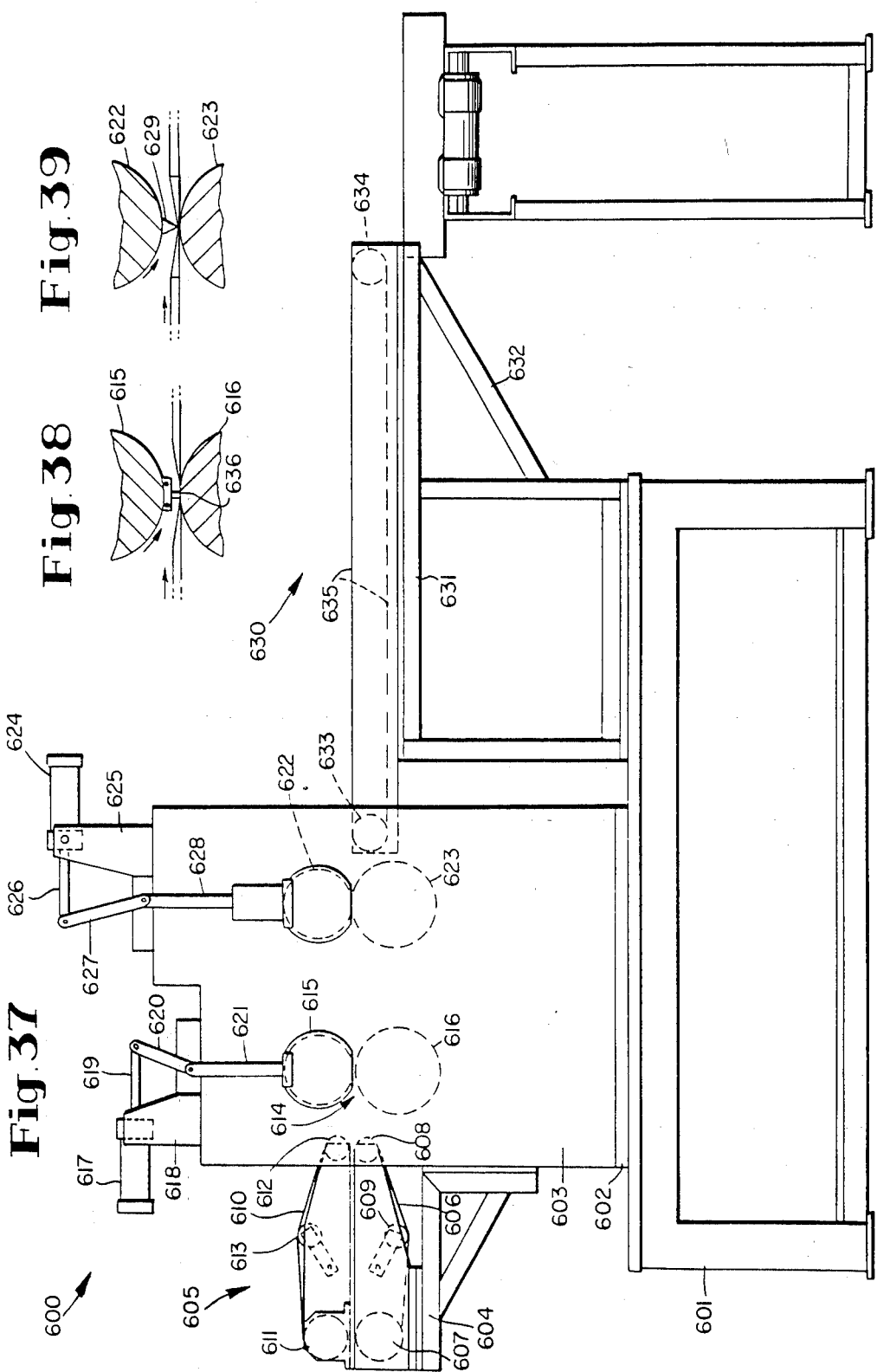

ABSORBENT PADS, INCONTINENCE CARE PRODUCTS AND METHODS OF PRODUCTION

CROSS REFERENCE TO RELATED APPLICATION(S)

This application incorporates by reference the disclosure(s) of, and claims the benefit(s) of the filing date(s) of, the following applications: No. PCT/US82/00312, filed Mar. 10, 1982.

TECHNICAL FIELD

This invention relates to absorbent pads useful for the care of urinary incontinence and other applications, combinations of such pads with briefs, and methods of making such pads.

BACKGROUND OF THE INVENTION

The urinary incontinence care products available on the market today range from enlarged versions of the familiar disposable infant diapers to cumbersome pants arrangements, with many variations between these extremes. Some of the products are effective against leakage and odor emission, but are difficult to dispose of and/or cumbersome and/or heavy and/or uncomfortable to wear for long periods whether wet or dry. Others, which are less cumbersome, heavy or uncomfortable, appear to be less effective against leakage and odor emission. Thus a need exists for urinary incontinence care products or systems which are smooth and close fitting rather than bulky, are readily disposable, exert relatively little localized pressure on the skin and yet effectively stay in place, and are light in weight and effective against leakage and emission of odors.

The present invention arose in part from attempts to produce satisfactory urinary incontinence care pads from absorbent materials which are capable of being formed into layers and which are highly absorbent, i.e. capable of absorbing at least about 5, more particularly at least about 15, and most preferably at least about 35 times their own weight of water or urine. One example of such layers of highly absorbent material is a commercially available "sandwich" comprising a central film of polymeric material, such as for instance lightly cross-linked, partially saponified polyacrylate or polyacrylamide that is water absorbent (including water-swellable), having a cellulosic fiber layer on each of its major surfaces.

Heretofore, in the attempt to produce absorptive pads for the care of patients subject to urinary incontinence, it has been assumed that at least some patients would require a pad having both a large ultimate absorption capacity and a relatively high rate of absorption. For example, in severe applications, where sudden and major evacuations of liquid are likely, it is believed that a urinary incontinence care pad should be capable of absorbing, without substantial run off or loss of liquid, at least about 150, or 200, or 250 cc. or more of urine at evacuation rates of at least 5 or 10 or more cc. per second, and that the pad should have the foregoing absorption rate coupled with an ultimate capacity of at least about 200, or 250, or 300 or more cc.

Heretofore, attempts to obtain the desired capacity and rate by forming pads from commonly available high-absorbency sheet materials have proved disappointing. In those instances where high capacities were obtained, absorption rates proved inadequate. Thus, it has been indicated that when the above-mentioned high absorbency sheet materials are present in the pad in sufficient amounts to constitute about 50% or more of the total absorption capacity of the pad, inadequate absorption rates result.

Heretofore, various attempts have been made to improve the absorption properties of the above-mentioned highly absorptive materials. It is reported that the manufacturer of one form of such material considered the forming of holes in the material. However, it is understood that the attempt was abandoned due to fear of loss of absorbent material as a consequence of punching pieces of absorbent material out of the sheet, with consequent loss of ultimate absorption capacity. It is also understood that there was some experimentation with forming small pinpricks or slits in such layers of highly absorptive materials, but these proved to be of little if any benefit. It has also been reported that in order to obtain satisfactory results one must employ short slits of controlled length which open and then close after a period of absorption.

From the foregoing, it may be seen that a need remains for rate-enhanced, liquid absorbent pads having high absorption capacity, and if such pads are to be used in the care of urinary incontinence, there is a need for them to be compact and readily disposable, such as by flushing in a common toilet. The principal objectives of the present invention are to fulfill the above needs.

ABSORPTION RATE TEST

A simple test was devised to determine the absorption rates of composites comprising high absorbency layers, e.g. sheets, such as for example the above-described "sandwich" composites comprising partially saponified lightly cross-linked polyacrylate or polyacrylamide films. According to this test procedure, test liquid is poured at a controlled rate and in a predetermined amount over successive samples of pads supported on a mild incline, (e.g. about 15° to 20° from horizontal). The rate and amount are selected to substantially exceed the absorption rate capabilities of the samples, and the amount of test liquid which runs off each pad before it can be absorbed is recorded and subtracted from the total amount poured. The difference in each case indicates the absorption rate capabilities of the sample pad. Exploratory research performed with the aid of the foregoing procedure surprisingly resulted in the discovery of how to produce both excellent rate characteristics and more than adequate ultimate capacity in absorbent pads, resulting in improved pads which are useful, among other things, for the care of urinary incontinence.

SUMMARY OF THE INVENTION

According to the invention, the above-described needs have been met in part by forming an absorbent pad comprising at least one and preferably a plurality of layers of material, including at least one absorptive layer provided with openings to appreciably enhance the rate of liquid absorption of the pads. At least one such absorptive layer in the pad comprises water-absorbent (including water-swellable) material, which may be polymeric or non-polymeric, said material having the capability of absorbing at least about 5, preferably at least about 15 and more preferably at least about 35 times its own dry weight of clear water or other aqueous liquid.

The water-absorbent material is preferably present in the pad in a sufficient amount so that at least about 50% of the total liquid absorption capacity of said pad is present in said water-absorbent material. The pad may also include other layers of non-absorbent material or of material having a lower absorption capacity per unit weight than the first-mentioned absorbent material.

The amount of the first-mentioned absorbent material is preferably sufficient so that it constitutes at least about 60%, and more preferably from about 65 to 80%, of the total liquid absorption capacity of the pad. Said first-mentioned absorbent material may be present in an amount sufficient to provide even 90% or higher of the total liquid absorptive capacity of the pad, especially where lower absorption rates than may be desired for urinary incontinence devices can be tolerated.

The openings are formed by cutting around a portion, but not the entire periphery of the opening for forming hinge and flap members. The cutting lines, viewed in plan view, smoothly curve past the edges of the hinge portions to ends which diverge from one another for inhibiting tear propagation in the absorptive layer(s) adjacent to the hinge members.

Further, in accordance with the present invention, the pad is formed from one or more absorptive layers which include undulations comprising a plurality of bends formed in said layer(s) running lengthwise thereof for increasing the quantity of absorptive layer material which is available for absorption beneath a given area of the liquid absorption surface of the pad, or for assisting in retaining, restricting or directing the flow of liquid. Any suitable arrangement may be employed, a number of merely illustrative examples being provided by British published patent application No. 2,017,509 and by U.S. Pat. Nos. 3,525,337, 3,610,244, 3,653,382, 3,865,112, 3,903,889, 3,968,798 and 4,176,667.

According to this invention an absorbent sheet material is formed into an elongated shaped pad of greater width than thickness, having an upper major surface and a lower major surface, at least one of which is adapted for placement adjacent a wearer's body for receipt of urine. The absorbent sheet material is present in the pad in one or more layers which, as viewed in transverse cross-section, have an undulating characteristic. The undulations formed in the sheet material may be of any shape which is suitable to enhance the total effective area of absorbent sheet material available for absorption beneath a given area of the upper or lower major surfaces.

The undulations are arranged in the pad, and the pad is so positioned in briefs or other suitable holding garments or devices, so that the furrows and peaks or ridges formed by the undulations extend between the wearer's legs in a direction from front to rear. The undulations may be produced with or without creasing of the absorbent material. Moreover, the undulations may be produced with varying forms, such as by crinkling, pleating, or forming serpentine loops. According to one embodiment, the absorbent sheet material is pleated with folds which have inner creases and outer edges. These folds alternate in opposite directions to form a plurality of panels of substantially varying or preferably uniform width which are interspersed with said folds. The folds may be and preferably are arranged across substantially the entire width of the pad, so that the edges of alternate folds are presented upwardly at or adjacent one of the above-mentioned major surfaces and the edges of intervening folds are presented downwardly at or adjacent the other of said major surfaces.

At least one layer comprising said absorbent material is provided with openings formed as described in detail below, for appreciably enhancing the rate of liquid absorption of the pad. The openings have a sufficient average open area per opening and are distributed throughout a substantial portion of the available surface of the absorptive layer to provide an overall ratio of the total open area of said openings to the area of said portion (without deduction for the open area) in the range of about 0.002 to about 0.25, more particularly about 0.002 to about 0.20, preferably about 0.004 to about 0.15 and still more preferably about 0.008 to about 0.08. The open area per opening may for example be in the range of about 0.02 to about 1.3, more preferably about 0.05 to about 1 and more preferably about 0.15 to about 0.8 $cm^2$. The number of openings may for example be in the range of about 0.006 to about 0.3 or 0.4, more preferably about 0.006 to about 0.25, still more preferably about 0.01 to about 0.15 and most preferably about 0.1 to about 0.15 openings per $cm^2$ of the area of that portion of the material in which the openings are provided, it being understood that the openings may be present in all or only a portion of the absorptive layer comprising absorbent material and that the openings may be distributed throughout said portion or layer in a random or substantially uniform manner, or in a non-uniform manner intended to maximize rate of absorption in a particular section of the layer where extra absorption is desired or required. Where the openings are arranged in one or more discrete arrays which are collectively distributed over only a portion of the entire area of the layer, the area of said portion may be defined as the total area delineated by first tracing line segments intersecting with the centers of the outer-most openings in each array to define an individual "field" for each array, and then adding to each field a border equal in width to the average spacing of all openings in its respective array of openings. In those instances in which the openings are provided throughout the available area of an absorptive layer, the total surface area of the layer (without deduction for the open area) may be used. The openings referred to above may generally be of any shape provided that they have significant open area, and are therefore to be distinguished from slits, pinpricks or other openings which have been formed without folding back material to form a significant open area. Whether the openings conform to the above number and area criteria or not, folding back to form a hinge and flap construction retains the absorption capacity of the "hole" material in the resultant pad.

According to a preferred embodiment, the absorptive layer and other components of the pad are selected from among materials which do not retain their structural integrity when mildly agitated in liquid, such as for example the mild agitation normally encountered within the bowl of a common reservoir-type household toilet wherein the hydrostatic head of the water in the reservoir relative to that in the bowl, under static conditions, is about 60 cm. Thus, the pad preferably will have sufficient capability of undergoing appreciable or substantial disintegration under such agitation so that it is "flushable", i.e. it can readily be disposed of in such toilets with little or no danger of clogging.

According to a particularly preferred optional embodiment of the invention, any of the above-described pads or pads of other designs are combined with an elongated sheath portion, the latter being of suitable length and width and preferably having at least one opening or openable portion to facilitate removing wet pads therefrom. The sheath may or may not be, but preferably is, free of permanent connections between itself and the pad, but is of such width as to closely surround the pad. According to a particularly preferred embodiment, the sheath is of greater length than the pad and thus includes one or more extensions which extend beyond one or both ends of the pad for holding the pad in place in a brief or other holder.

The sheath portion may also be flushable but, according to one preferred embodiment of the invention, the sheath portion constitutes a water-pervious material which substantially retains its structural integrity on exposure to human urine. Particularly preferred for the sheath portion are non-woven or woven fabrics having sufficient open area between their fibers, strands or filaments and being formed of sufficiently non-absorbent material such as to prevent absorption of any substantial quantity of liquid by the sheath, e.g. polyester and/or polyolefin fibers, strands or filaments. A sheath portion so formed constitutes a convenient means for transporting a used absorbent pad from a pair of briefs or other holder to a disposal container or toilet. Such sheaths could in some cases be launderable and reuseable with disposable pads.

The above-described pads may be employed with or without briefs and have application to uses other than care of urinary incontinence.

In the care of urinary incontinence one may employ one or more absorbent pads capable of absorbing urine in the desired amounts and at the desired rate. For example one may employ a plurality of pads having in combination the desired capacity and absorption rate. It is however preferred to employ a single pad possessing the desired capacity and absorption rate. For example, in light duty applications, it is recommended that the pad or pads have an overall, ultimate absorption capacity of at least about 125, more preferably at least about 150 and still more preferably at least about 175 cc (cubic centimeters) of natural or synthetic urine. In more severe applications, for example where sudden and major evacuations are likely, it is recommended that the pad be capable of absorbing, without substantial run-off or loss of liquid, at least about 150, more preferably at least about 200, and still more preferably at least about 250 cc of natural or synthetic urine at an evacuation or application rate of at least 5 and preferably at least 10 cc per second. It is further recommended that pads for such severe applications should have an overall or ultimate absorption capacity of at least about 200, more preferably at least about 250, and still more preferably at least about 300 cc. In either case, ultimate capacity should be measured by applying test liquid at or below the maximum rate at which the pad or pads will accept liquid.

The urinary incontinence care brief employed in the present invention comprises a belt portion and a holder portion. The belt portion has posterior, side and front sections and is of sufficient length for extending about the posterior, sides and front of a wearer's abdomen. The holder portion has rearward, central and forward zones. These zones are of sufficient combined length for extending from the posterior section of the belt portion between the legs of the wearer to the front section of the belt portion. The brief also includes retaining means for removably retaining an absorbent pad in position upon said holder portion for absorbing urine evacuated by the wearer.

The method of the present invention comprises forming an absorbent pad comprising at least one but preferably a plurality of layers of material including at least one absorptive layer. At least one such absorptive layer in the pad comprises water-absorbent (including water-swellable) material, which may be polymeric or non-polymeric, said material having the capability of absorbing at least about 5, preferably at least about 15 and more preferably at least about 35 times its own dry weight of clear water or other aqueous liquid. At least one layer comprising said absorbent material is provided with openings, as above described, for appreciably enhancing the rate of liquid absorption of the pad.

Such openings are formed in a randomly distributed or patterned manner in the absorptive layer. A plurality of bends is formed in said layer running lengthwise thereof and spaced at intervals across the width of said layer, for forming said layer into an elongated pad stock of greater thickness and narrower width than said layer. The pad stock is eventually cut transversely at longitudinal intervals to form pads of predetermined length therefrom.

In accordance with the invention the above-mentioned openings are formed by cutting through the material of said layer or layers along a portion but not all of the perimeter of the respective openings, thereby forming of said layer(s) one or more hinge and flap members at the respective openings. By means of force applied through the resultant openings, said flap members are displaced outwardly relative to the layer(s). Preferably, said flap members are then also displaced further in a direction inward relative to said layer(s) of absorbent material and the flap members are pressed against portions of one or more layers adjacent the respective hinges while leaving said openings substantially open. The first-mentioned displacement is preferably performed by means of members projected through the resultant openings, displacing the flap members outwardly relative to said layer(s). A preferred mode of performing the second displacement is rolling said layer(s) between rollers, thereby causing further displacement of the flap members in a direction inward relative to said layer(s).

A particularly preferred mode of operation is longitudinally advancing the absorbent layer material in strip form to contact a first cutting roller which cuts the openings in the hinge and flap configuration and continuing the advance of the cut strip across the surface of a second roller with outwardly projecting members driven in synchronization with the cutting roller, to perform the first-mentioned displacement. The strip is then preferably rolled between rollers as described above.

By forming the hinge portions by cutting lines which, as viewed with the layer(s) in plan view, gently and smoothly curve past the edges of the hinge portions to ends which diverge from one another, one can inhibit tear propagation in the layer(s) in and/or adjacent the hinge members. In this connection it is considered beneficial if the gently, smoothly curved portions of the cutting lines include the transitions from the openings per se to positions alongside the hinge portions and/or if the ends of the cutting lines diverge from one another in opposite directions, especially parallel to the bending lines of the hinges. Where coincident hinge and flap type openings are formed simultaneously in the several layers of a moving composite and the several flaps at each opening through the composite are displaced outwardly together, they cooperate to bind the layers together and promote coordinated movement of the several layers. This is particularly useful where some of the layers are caused to move by directly applied driving force and others, for example inner layers in the composite, receive such driving force indirectly, i.e. through frictional engagement with other layers. For best results in attaining such binding, it is recommended that the hinge be formed with a lesser width, measured along the hinge bending line, than the maximum width of the opening, measured parallel to said bending line. When the hinge is of lesser width than the opening and the flap member is displaced to project away from the composite, it can then effectively lock together the layers in the composite during transport. When the hinge members are formed by cutting lines which curve in the above-described manner, this imparts extra strength to the hinge members which can be useful in performing the above-described binding function.

In accordance with the invention a plurality of bends in the above-mentioned layer(s) running lengthwise thereof and spaced at intervals across the width of said layer(s) are formed, thus providing an elongated pad stock of greater thickness and narrower width than said layer(s). Best results have been obtained by bending at least one layer as it advances longitudinally in strip form through two arrays of rails or other forming members which, as scanned from edge to edge in transverse cross-section, cause the strip to contract laterally while alternatively displacing adjacent portions of the contracting strip in opposite directions perpendicular to the major surfaces of the strip, thereby forming an undulating or zig-zag pattern. When the previously described first displacement (and second displacement, if any) are performed in such a manner that the flaps are left extending away from the layer(s) from which they are formed, and the layer or layers are formed into an undulating pattern as above described, the flaps can act as spacers between adjacent undulations for promoting rapid access of incoming liquid to the length and depth of the undulations, thus promoting a high absorption rate.

According to another preferred embodiment, the method includes bringing pad stock, prior to or after cutting of the pad stock, into contact with sheath material, described above, which is wider than said pad stock, causing the pad stock and sheath material to advance together longitudinally and bending the sheath material along a longitudinal line or lines for surrounding the pad stock as viewed in transverse cross-section.

When it is desired to form a sheath with extensions for securing and handling the completed pad, as mentioned above, the above-described transverse cutting of the pad stock is performed prior to contacting the pad stock and sheath material. Then the cut sections of pad stock are advanced into contact with the sheath material while the latter is advancing longitudinally at an accelerated rate relative to the rate of advancement of the pad stock during cutting, thereby causing the sections of pad stock to travel longitudinally in contact with the sheath material with a predetermined space between these sections which is about twice the length of the desired sheath extensions.

When the pad stock is cut transversely into sections as described above, a preferred embodiment of the invention includes applying compression during cutting to a narrow band of material adjacent the trailing edge of each cut. Sufficient compression is applied for causing collapsed and overlapping undulations and/or other layers in the pad stock to cling to one another with sufficient adherence to form a coherent leading edge at the front of each cut pad section which retains substantial structural integrity during subsequent advancement of the pad sections. Then the pad sections with coherent leading edges are advanced longitudinally into contact with sheath material while the latter is advancing longitudinally at an accelerated rate relative to the rate of advancement of pad stock during the transverse cutting of the pad stock. Thereafter, the pad stock sections travel longitudinally with the sheath material and the sheath material is cut transversely in the above-described manner.

The method invention includes a preferred mode of completing a sleeve-like sheath by the operation of securing its marginal edges together in overlapping or other relationship by any suitable technique such as sewing, or bonding through fusion, and/or adhesively bonding adjoining portions of such edges. According to a preferred embodiment the sheath, with continuous running length pad stock or with cut pad stock sections within it, is advanced longitudinally in strip form and the advancing marginal edges of the sheath material are brought into contact with one another and are caused to project outwardly relative to the nearest major surface of the pad stock during, and possibly also prior to, such securing operation.

Another optional but preferred embodiment commences subsequent to formation of the pad stock in strip form but prior to application of the sheath material. The pad stock is brought into contact with liquid permeable material in strip form which is wider than the pad stock. The pad stock and liquid permeable material are then advanced together longitudinally and the permeable material is bent along one or more longitudinal lines for encircling the pad stock as viewed in transverse cross-section, thereby forming a wrap of such permeable material around the pad stock. The above-described cutting operation is then applied to said pad stock and wrap together to form pads of predetermined length. The resultant wrapped pads are brought into contact with a strip of sheath material which is wider than said pads, the sheath material being bent along a longitudinal line or lines for encircling the pads as viewed in transverse cross-section. The marginal edges of the sheath material are then secured to one another for forming sleeve stock surrounding the wrapped pads. Optionally, transverse seals are formed in said sleeve stock adjacent at least one end of each pad.

Very rapid production of pads may be attained by an optional but preferred embodiment which includes advancing said layer of absorptive material longitudinally in strip form while making the randomly distributed or patterned openings therein at locations distributed substantially throughout the length of the strip; forming said openings by cutting through said strip along a portion but not all of the perimeter of the respective openings, thereby forming of said strip material one or more hinge and flap members at the respective openings; by means of force applied through the resultant openings, displacing said flap members outwardly relative to said strip; causing further displacement of said flap members in a direction inward relative to said strip and pressing said flap members against portions of the strip adjacent the respective hinges while leaving said openings substantially open; while advancing said strip longitudinally, forming a plurality of bends in said strip running lengthwise thereof and spaced at intervals across the width of said strip, for forming said strip into an elongated pad stock of greater thickness and narrower width than said strip; subsequent to formation of said pad stock, while advancing said pad stock longitudinally, bringing into contact with said pad stock a strip of liquid permeable material which is wider than said pad stock, causing said pad stock and liquid permeable material to advance together longitudinally, and bending the liquid permeable material along longitudinal lines for encircling the pad stock as viewed in transverse cross-section, thereby forming a wrap of liquid permeable material around said pad stock; and, while advancing said pad stock and wrap together longitudinally, cutting pads of predetermined length therefrom.

It is also optional but preferred to combine the operations of the preceding paragraph with further steps for rapidly forming sheaths with extensions about the resultant pads. Thus, subsequent to the cutting of said pads, they are brought into contact with a strip of sheath material which substantially retains its structural integrity when exposed to liquid and which is wider than said pads. The pads and sheath material are caused to advance together longitudinally at an accelerated rate relative to the rate of advancement of said pad stock and wrap during cutting, thereby causing said pads to travel longitudinally with a predetermined space therebetween which is about twice the combined length of sheath extensions to be formed subsequently. This embodiment also includes: bending the sheath material along a longitudinal lines or lines for encircling the pads as viewed in transverse cross-section; continuously securing the sheath material in surrounding relationship with the advancing pads for forming continuous running length sleeve stock surrounding the pads; and, as the sleeve stock and the pads advance longitudinally, transversely cutting said sleeve stock at longitudinal positions intermediate said pads, thereby forming absorbent pads within sheaths having sheath extensions extending a sufficient distance beyond the ends of said pads for handling and/or securing said pads and sheaths.

BRIEF DESCRIPTION OF THE DRAWINGS

FIG. 5 is a perspective view of a sheet of absorbent layer material useful in forming pads in accordance with the present invention.

FIG. 6 is a perspective view of a composite useful for forming pads in accordance with the invention, and containing at least one absorptive layer similar to that shown in FIG. 5.

FIG. 7 is a fragmentary view of the end of a composite, for example the composite of FIG. 6, which has been shaped to form undulations therein.

FIG. 8 is a perspective view of a pad formed in accordance with the invention and comprising undulations, for example the undulations shown in FIG. 7.

FIG. 9 is an exploded view in perspective of layers of absorptive material forming a composite for an alternative to the form of pad disclosed in FIGS. 5 through 8.

FIG. 10 is a top plan view of a pad formed using the composite of FIG. 9, a portion of the pad being broken open to show the composite within.

FIG. 11 is a bottom plan view of the pad of FIG. 10 showing portions of an exterior wrapper being folded back to disclose the composite of FIG. 9 within.

FIG. 12 is an exploded view in perspective showing a composite design for forming a pad in accordance with the present invention.

FIG. 16 is a partly schematic side elevation of the pad raw materials dispensing section of apparatus for carrying out the methods of the present invention.

FIG. 17 is a side elevation of the aperture forming section of apparatus for carrying out the methods of the present invention.

FIG. 18 is an enlarged perspective view of a portion of the apparatus of FIG. 17 showing a cutter roller surface and absorbent material cut thereby.

FIG. 18A is an enlarged portion of the surface of the cutting roller of FIG. 18, in plan view, showing one of the cutting dies formed thereon for cutting hinge and flap members.

FIG. 19 is an enlarged portion of the apparatus of FIG. 17 showing a strip of absorptive layer material and the nip of a knock-out roller and mating pocket roller for displacing hinge and flap openings cut by the dies of FIGS. 18 and 18A.

FIG. 20 is an enlarged portion of the apparatus of FIG. 17 illustrating the strip with displaced hinge and flap members entering and passing through flattening rolls for further displacement.

FIG. 21 is a partly schematic side elevation of the apparatus including a pad stock bending section which receives material from the apparatus of FIG. 17 and a wrapping section.

FIG. 22 is a sectional view taken along section line 22—22 in FIG. 21 showing absorptive layers entering arrays of bending rails in the bending section.

FIG. 23 is a sectional view taken along section line 23—23 in FIG. 21, depicting the layers of absorptive material deflecting into a zig-zag configuration in the bending section.

FIG. 24 is a sectional view taken along section line 24—24 in FIG. 21, illustrating a further development of the zig-zag configuration of FIG. 23.

FIG. 25A is an enlarged portion of FIG. 25 showing the tip of a disc in the aforementioned array and a mating groove in the cooperating cylinder.

FIG. 27 is a sectional view taken along section line 27—27 in FIG. 21 showing commencement of bending of a tissue wrap around the pad stock received in the bending section of the apparatus from the confining rollers of FIG. 26.

FIG. 28 is a sectional view taken along section line 28—28 in FIG. 21 showing a further development of the bending shown in FIG. 27.

FIG. 29 is a sectional view taken along section line 29—29 in FIG. 21 depicting the completion of the bending of FIG. 28, so that the pad stock is encircled with the tissue wrap.

FIG. 30 is a partly schematic side elevation of the pad cutting section and sheath material application section which receive wrapped pad stock from the apparatus of FIG. 21.

FIG. 31 is an enlarged portion of FIG. 30 showing details of the nip of the cutting roller and cooperating cylinder which receive wrapped pad stock from the FIG. 21 apparatus.

FIG. 31A is an enlarged, fragment of FIG. 31, showing a transverse cross-section of the profile of the cutting edge of the cutting roller.

FIG. 37 is a partly schematic side elevation of the sleeve stock transverse heat-sealing and cutting section which receives pad stock surrounded by sleeve stock from the apparatus of FIG. 30.

FIG. 38 is an enlarged, partially broken-out portion of FIG. 37 illustrating the nip of the sleeve transverse heat-sealing device and its cooperating cylinder, contacting and bonding the sleeve stock intermediate the ends of the pads.

FIG. 39 is an enlarged, partially broken-out portion of FIG. 37, showing a cutter roller and its cooperating cylinder for cutting the sleeve stock with pads therein to separate individual pads surrounded by sheath material with sheath extensions to facilitate securing or handling of the pads.

DETAILED DESCRIPTION

Figure 1:
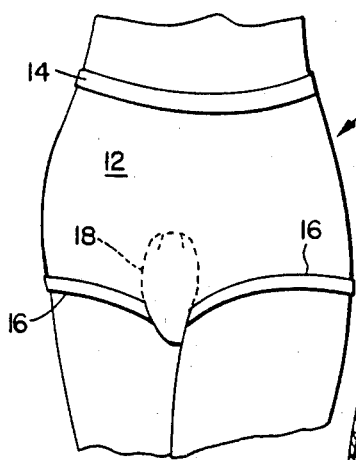
FIG. 1 shows a perspective view of the torso of an individual wearing incontinence care briefs according to the present invention.

The following is a detailed description of certain preferred embodiments of the invention. Like reference numerals identify like elements in each of the several figures of the accompanying drawings.

In FIG. 1, a modified pair of briefs 10 is illustrated as it would appear on a person's body. Although briefs 10, as illustrated, preferably are of the type which extend from the person's upper thigh to the waist, those skilled in the art will understand that the invention also may be applied to other styles of pants such as bikini pants and the like. The body 12 of pants 10 may for example be made from a suitable knit or woven fabric made from such fibers as cotton, nylon, polyester or the like. At the waist, an elastic band or belt portion 14 is provided which includes posterior, side and front sections and may be approximately 1 to 2.5 cm in width and around the leg openings, no-elastic high stretch bands 16 are preferably provided, which also may be approximately 2.5 cm in width.

Figure 3:
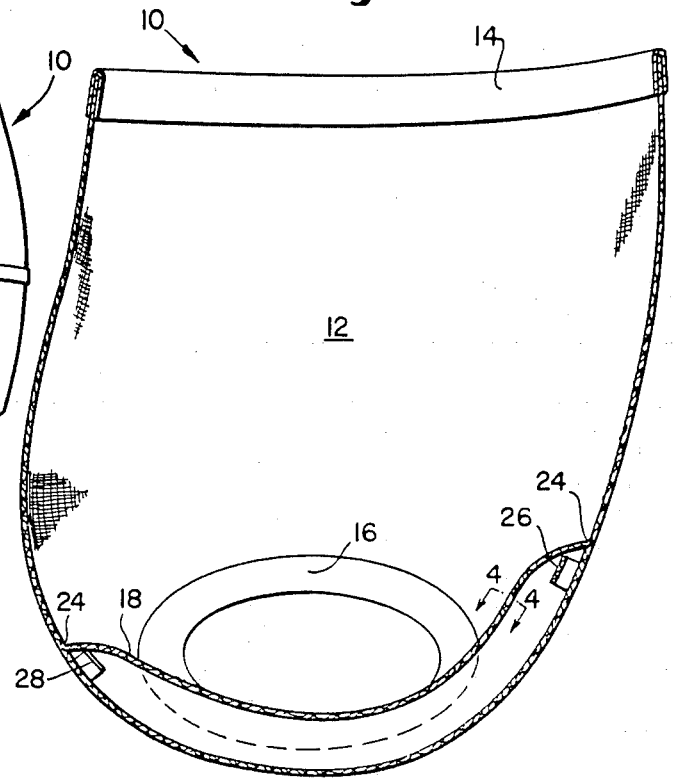
FIG. 3 is a sectional view taken along section line 3—3 of FIG. 2 showing the placement of a moisture impervious panel in the briefs.
Figure 2:
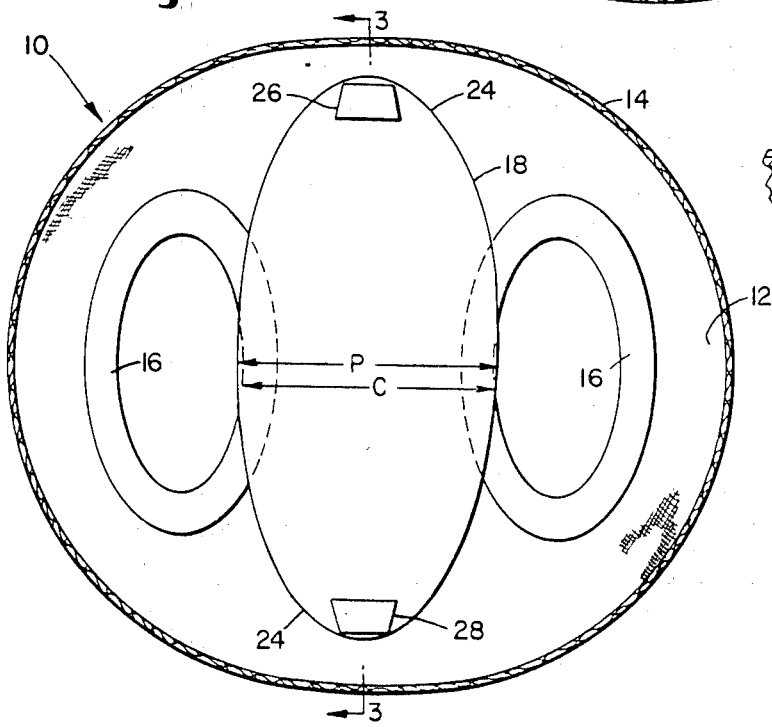
FIG. 2 shows a top view of the briefs of FIG. 1, showing the appearance of the interior of the briefs when viewed through the waist opening.
Figure 4:
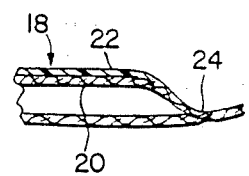
FIG. 4 is a fragmentary sectional view taken along section line 4—4 of FIG. 3, depicting a joint formed between the body of the briefs and the moisture impervious panel.

As shown in FIGS. 2 through 4, the interior of briefs 10 is provided with a holder portion that includes rearward, central and forward zones on which are mounted a moisture impervious laminated panel 18. This panel extends from a position rather low in the seat of the briefs, through the crotch or holder portion between the leg openings 16 and upward to a position rather high on the front of the briefs. As illustrated, panel 18 has an essentially elongated, oval geometry and comprises a lower layer 20 of a suitable knit or woven fibrous material such as nylon. A liquid impervious upper layer 22 of a thermoplastic or thermosetting polymeric film material such as vinyl is impregnated into or laminated to layer 20. As a result, panel 18 is somewhat stretchy but usually less stretchy than the body 12 of briefs 10. In a pair of briefs suitable for wearing by persons having waist sizes in the range of about 56 to 81 cm, the crotch width C shown in FIG. 2 preferably is approximately 15.3 cm, including the leg bands. In such a case, panel 18 preferably has a width P of approximately 15.9 cm and a length of approximately 31 cm. Panel 18 is positioned so that as viewed in its longitudinal cross-section, the upper edges of its front and rear ends respectively appear approximately 21 cm and 10 cm above the bottom center portion of the crotch, measured along the profile of the panel.

When panel 18 has been positioned in this manner within a pair of briefs, it is joined to the briefs by any suitable means such as sewing or gluing and the like. Stretching of body 12 during such joinder is minimized to prevent puckering at the edges of panel 18. Preferably, panel 18 is attached using a peripheral heat joint 24 of approximately 1/8 to ⅛ inch in width. Joint 24 may be formed using dielectric heat sealing equipment in which the periphery of panel 18 and a narrow portion of body 12 are compressed between dies and the temperature of thermoplastic layer 22 is elevated until the plastic flows through the cloth lower layer 20 of panel 18 into the interstices of the cloth forming the body 12 of the briefs to form a narrow band 24 of interlocked plastic and fabric, as shown in FIG. 4.

After panel 18 has been joined to body 12 of briefs 10, a pair of elastic loops 26, 28 is stitched through panel 18 and body 12 at the front and rear edges of the panel, as shown in FIGS. 2 and 3, to act as retaining means for attachment of an incontinence pad to be worn within the briefs. The loops could also be attached to panel 18 before joint 24 is formed. To ease insertion of the sheath extensions which may be provided at each end of the incontinence pad, loops 26, 28 preferably are approximately 1.3 cm wide and 3.8 cm in length at their lower edges and 3.2 cm in length at their upper edges.

In general, the above described briefs may be used with any suitable pad including those presently known and those introduced hereafter. However, certain types of pads and features of pads, and combinations of such pads with briefs in accordance with the invention, constitute preferred embodiments which in themselves are considered to be inventions. Some of these will be discussed in greater detail hereinafter.

The pads provided in accordance with the present invention are characterized by the property of absorbing liquids. This includes anatomical fluids such as urine and non-anatomical fluids such as water and other polar and non-polar fluids. However the primary and preferred application for these pads is in the absorption of urine and/or other anatomical fluids. Recommended absorption capacities for such pads are set forth above under the heading "Summary of the Invention."

The absorptive pads used in the practice of the invention may include a single layer of liquid absorptive material. The preferred pads include, however, a plurality of layers of liquid absorptive material, referred to herein as "composites," which may include similar and/or dissimilar layers of absorptive and non-absorptive material, including layers which are and/or are not bonded to one another. The various layers may differ in their respective absorption rates and capacities.

A wide variety of materials are available, which are capable of being formed into layers and which are highly absorbent, i.e. capable of absorbing at least about 5, more particularly at least about 15 and most preferably at least about 35 times their own weight of clear water. Among the applicable materials are those which are capable of absorbing the same ratios of natural or synthetic urine, such as a 1% by weight saline (e.g. NaCl) solution. The urine capacities of these materials are usually less than, but may be equal to or greater than, their capacities for clear (i.e. pure) water.

Examples of such materials may be found in British Patent Specification No. 1,515,768 and in U.S. Pat. Nos. 3,890,974, 3,903,232, 3,935,099, 3,981,100, 3,985,616, 3,997,484, 4,069,821, 4,090,013, 4,093,765, 4,117,184, 4,144,886, 4,155,893 and 4,172,066, and in the following publications: B. Ranby and C. Rodehed, Polymer Bulletin, Vol. 5, 87, 1981; R. Mehrotra and B. Ranby, J. Appl. Pol. Sci., Vol. 21, pages 1647 and 3407, 1977 and Vol. 22, page 2991, 1978; and M. 0. Weaver, et al, J. Appl. Pol. Sci., Vol. 15, page 3015, 1971 and Appl. Pol. Symposium 25, page 97, 1974, and in other documents mentioned in the foregoing publications and patents.

Such highly absorbent materials may be in the form(s) of particles, fibers, filaments, cellular solids, films and/or other forms, including both polymeric and non-polymeric material. When such materials are formed into or supported in, on or between sheets, certain of them are sometimes referred to as "hydrophilic paper," among which are included fibrous sheets (including batts and webs) that contain particles, fibers, films and/or other forms of natural and/or synthetic polymeric or non-polymeric material that is water swellable or water soluble. While it is preferred that at least the major proportion of the absorption capacity of the pad be provided by absorbent material(s) which are natural and/or synthetic polymeric material(s), and that the major weight proportion of such polymeric material(s) should be substantially water-insoluble, substantially swellable and substantially hydrophilic in the pads as manufactured, or prior to use, the use of water-soluble and lower molecular weight materials in fabricating the pads is not excluded. For example, it is known to convert water-soluble gums and polymers to substantially insoluble and swellable absorbents in situ, such as when a urinary incontinence care pad is wetted in use, by providing in the pad a cross-linking agent whose cross-linking action is triggered by moisture and/or by other components of body fluids, including urine. For illustrations, see U.S. Pat. Nos. 3,903,889 to Torr and 4,333,464 to Nakano.

The polymeric material may be of any suitable class or description, such as for instance lightly cross-linked homo- or co-polymeric acrylamides or acrylates, illustrative examples of which are the Dow Water Absorbent Polymer films, sold by Dow Chemical Company of Midland, Mich. in its various Dow Water Absorbent Laminate Products, and Favor SAB-82 polyacrylic homopolymer sold by Chemische Fabrik Stockhausen GmbH of Krefeld, West Germany. Preferred examples include various modified starches, such as graft polymers with starch backbones, having substantial proportions of their hydroxyl groups modified or replaced with moieties which may be of short to long chain length. Such moieties may for example include polyether or polyacrylic chains, including those which provide reactive carboxyl groups in the resultant modified starch. A small proportion of the carboxyl or other reactive groups present on the graft polymer side chains may or may not be reacted with organic and/or inorganic di- or poly-functional cross-linking agents, and any desired additional proportion of the carboxyl groups, including preferably major proportions thereof, may be reacted with organic and/or inorganic neutralizing materials, such as NaOH, KOH, amines and other bases. Particularly preferred are the starch backbone graft polymers having polyacrylic side chains such as SGP-147 (formerly a Henkel product) sold by Grain Processing Corporation of Muskatine, Iowa and San-wet IM 1000, sold by Sanyo Chemical Industries of Kyoto, Japan. However, persons of ordinary skill in the art will readily recognize that a wide variety of other forms of absorptive layer material may be employed in the pad of the present invention.

By way of example, the invention may be applied to a "sandwich" formed of swellable polymeric material positioned between two layers of cellulosic material which may support and/or protect the polymeric material. The most preferred example is a laminate known as Sap-sheet 4000-S(W), containing the above-mentioned San-wet IM 1000 and supplied by Sanyo Chemical Industries. In this product, the San-wet IM 1000 is supported between layers of tissue having little or no wet strength, so that when gelled, it is flushable.

The product, when used in accordance with the present disclosure, results in pads having excellent absorption rate and capacity, possibly up to about 65 cc of urine per gram of dry weight of sandwich material used. By way of further example, the invention may be applied to the above-mentioned Dow Water Absorbent Laminates disclosed in U.S. Pat No. 4,117,184 issued Sept. 26, 1978 to R. E. Erickson et al and assigned to the Dow Chemical Company, the entire disclosure of which is hereby incorporated herein by reference. The Erickson patent discloses a "sandwich" comprising a film of polymer that is water-swellable or gelable (i.e. forms a hydrated gel) sufficiently covered on at least two of its major surfaces with cellulosic fiber layers for imparting additional body or strength to the film and preventing blocking, as well as, reportedly, for protecting the polymer from environmental moisture. Preferably, this material has been crush-treated in accordance with the disclosure of U.S. Pat. No. 4,293,609 issued Oct. 6, 1981 to R. E. Erickson and assigned to Dow Chemical Company, said disclosure being incorporated herein by reference, and may also have been apertured during the manufacturing process. Some forms of this sandwich are said to have the property of absorbing at least 50 times their original unswelled weight of clear water, with correspondingly lower ratios being exhibited with urine and other saline solutions.

The Sanyo and Dow sandwiches may be used in combination. For example, two or more layers of each can be arranged one on top of the other in an alternating fashion. Where equal weights of the Sanyo and Dow sandwiches are present, it appears possible to absorb 45–50 cc of urine per gram of dry weight of sandwich material used. The preferred manner of using the Dow, Sanyo and other highly absorbent sheet materials is to form them into a composite with one or more additional discrete layers of absorbent sheet material which are not part of the sandwich(es). According to one embodiment, plural sheets of the sandwich material are separated by sheets of lower liquid absorption capacity per unit of weight, such as tissue or wadding or other absorbent materials with good capillary transfer values, such as light-weight non-wovens and bonded webs. Preferably such discrete layers include one or more layers of paper which is not bonded to the sandwich(es) and which is interleaved with sheets of the sandwich material in nesting relationship.

In a preferred embodiment of the pad comprising a combination of the absorptive sandwich material, as identified above, and one or more sheets of absorptive capacity lower than said sandwich, at least about 50%, preferably at least about 60%, and still more preferably from about 65% to about 80% of the total liquid absorptive capacity is present in the water-swellable polymer.

FIGS. 5 and 6 illustrate one form of composite which may be used in making a pad according to the invention. FIG. 5 discloses a single sheet 105 of the Sanyo or Dow sandwich material, having the capacity to absorb about 35 or more times its own weight of natural or synthetic urine or other saline solutions. The Dow sandwich material has heretofore been commercially available in forms which included tiny openings or pinpricks, but was considered deficient in absorption rate for use as the primary absorption medium in urinary incontinence pads. In accordance with the description under "Summary of the Invention", said sheet 105 is provided with circular openings 106 distributed in a substantially uniform manner throughout its total area, extending between the upper and lower major surfaces of the sheet. The openings are formed by punching, so that the material encountered by the punch is completely removed from the sheet. In this example, the open area per opening is about 0.317 cm$^2$, the number of openings per cm$^2$ of total sheet area is about 0.06, and the open area per unit area of said sheet is about 0.02.

As shown in FIG. 6, a composite 110 is formed by placing two sheets 105A and 105B of the sandwich material 105 of FIG. 5 between a pair of similarly sized sheets 107, 108 of ordinary tissue or wadding material. The sheets 105A and 105B in FIG. 6 have the openings (not shown) which are depicted in FIG. 5. The sheets 107, 105A, 105B and 108 may be secured together in any suitable fashion, such as by stitching, gluing, edge-taping or otherwise, and may, if desired, be provided with an outer layer of substantially water-proof or water-insoluble woven or non-woven fabric, preferably hydrophobic fabric. The composite shown in FIG. 6 may be used in the planar mode shown therein, or may be used as a basis for forming a variety of different kinds of pads. According to a particularly preferred specie of the present invention, the pad is formed from absorptive layers which have been folded as described above under "Summary of the Invention".

The foregoing is illustrated for example by FIGS. 7 and 8, which show the composite 110 of FIG. 6 having been folded to form undulations 113. The word folded is used in a broad sense which does not require but does contemplate the possibility of creasing of the layers of material in the composite. The resultant undulations comprise concave and convex portions 115 and 114, respectively, the former defining ridges interspersed with furrows 116. As shown in FIG. 8 the composite 110 with its undulations 113 may be secured at its ends in any suitable manner, such as for instance by taping, stitching, cementing or otherwise.

FIGS. 9–11 illustrate a still more preferable form of pad. In this embodiment a composite 130 is formed of outer layers 132 and 133 of absorptive material, such as the sandwich material described above, separated by an intermediate layer 131 of ordinary tissue or wadding which is not included in the sandwich material, nor is it necessarily bonded or otherwise attached to the sandwich material. In this embodiment, all three sheets are provided with openings as above described and the openings 134 are preferentially positioned at or near the ridges formed by undulations 135 having convex and concave portions 136 and 137 and defining furrows 138 between them. Openings may also be preferentially formed at or near the bottoms of the furrows. Such positioning of the openings can be of assistance in imparting flexibility to the pad. To complete the pad composite 130 is wrapped with an outer wrap of two plies of tissue or wadding 139 as shown in the top plan view of FIG. 10. A portion 140 of the tissue plies 139 is torn away and folded back (merely for purposes of illustration) to show composite 130 within. The outer wrap 139 has ends 141 and 142, the latter being folded over the former as shown in the bottom plan view of FIG. 11. For purposes of illustration only, portions 141A and 142B of outer wrap 139 are folded back in FIG. 11 to expose composite 130 and the openings 134. Note that the outer wrap 139, when closed, tends to obscure or conceal the openings and undulations, which may impart greater esthetic appeal to the pad.

Figure 13:
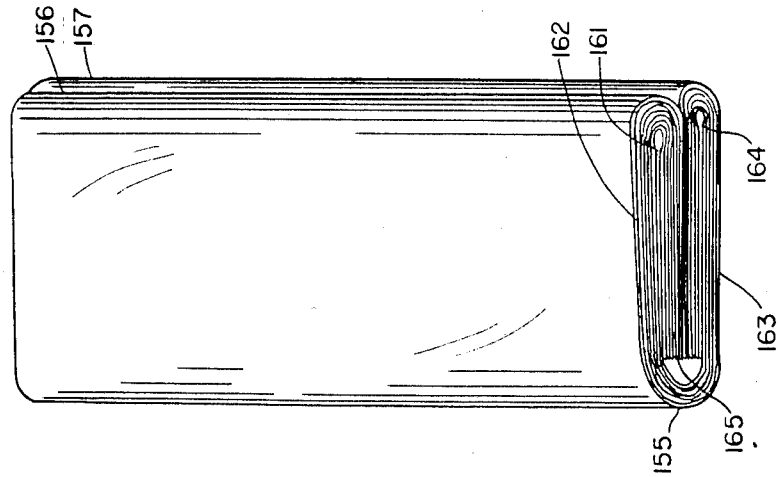
FIG. 13 is a perspective view showing a pad formed in a tri-fold configuration employing the composite of FIG. 12.

Assembly of another preferred form of pad is illustrated by FIGS. 12 and 13. A composite 145 is formed of a stack of five layers, including two layers 147 and 148 of hydrophilic paper separated and covered, above and below, with tissue or wadding layers 150, 146 and 149, respectively. Note that the three central layers 147, 148 and 150 are all provided with openings as above described, except that in this embodiment the openings 151A in the given absorptive layer, e.g. central tissue layer 150, are staggered, e.g. offset laterally or horizontally, in respect to openings 151B formed in an adjacent absorptive layer or layers, e.g. hydrophilic paper layers 147 and 148. The openings in adjacent layers may or may not coincide with one another, but it appears that a coincident arrangement may be beneficial from the standpoint of enhancing the absorption rate of the resultant composite. Composite 145 may then be folded into a tri-fold configuration as shown in FIG. 13, along folds 155, 156 and 157, dividing it into four stacked quarters 161, 162, 163 and 164, and hiding the ends 165 of the sheets in the composite within the body of the resultant folded member. This pad, as well as the pads of FIGS. 5–6, 7–8 and 9–11 may be provided with woven or non-woven water-insoluble outer sheaths as above described, and these may be formed of hydrophilic and/or hydrophobic fibers, including polyesters and/or polyolefins, the latter being treated with wetting agents if desired.

Figure 15:
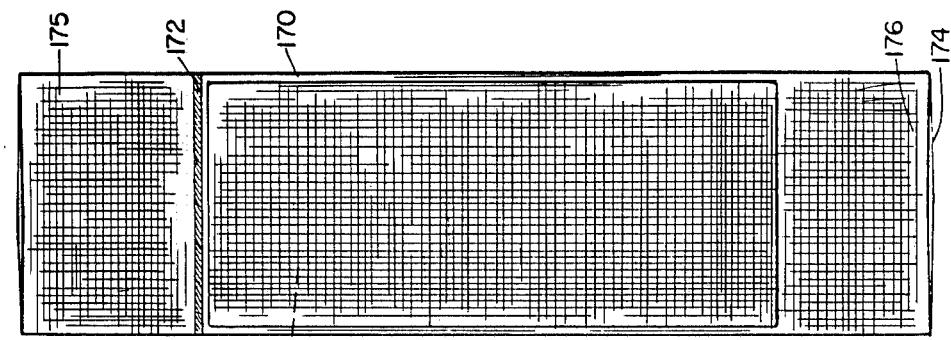
FIG. 15 is a top plan view of the pad of FIG. 13 within a sheath.
Figure 14:
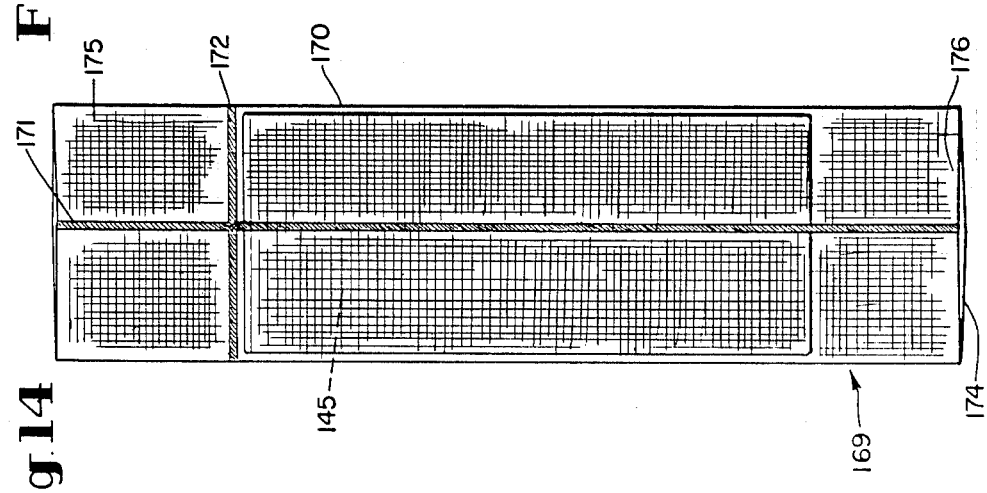
FIG. 14 is a bottom plan view of the pad of FIG. 13 within a sheath.

FIGS. 14 and 15 contain an illustrative embodiment of a sheath 169 according to the invention. A lightweight open mesh fabric 170 of hydrophobic, heat-sealable polyolefin filaments is formed into a tubular member. By way of further example, one may use any of the sheath fabrics disclosed in U.S. Pat. Nos. 3,395,708, Hervey, col. 3, l. 2–7; 3,561,447, Alexander, col. 2, l. 36–43; 3,903,889, Torr, col. 5, l. 8–13; and 3,939,836, Tunc, col. 6, l. 28–33. Formation of the tubular member may be accomplished, for example, by folding a running length of said fabric along substantially its longitudinal center line to bring the longitudinal edges thereof into substantial juxtaposition and bonding said edges together by compressing and heating said material in a continuous or discontinuous elongated region 171 extending adjacent said edges and fusing the folded portions of the material together in said region.

If the sheath material is not water dispersible, as taught for example in the above-mentioned Tunc patent, it may be desirable to provide for discharge of the sheath contents into a toilet, followed by separate disposal of the sheath. This may be accomplished for example by providing an opening or openable portion in the sheath. Both ends of the sheath may be left open for the discharge of wet pads. However, in the present preferred embodiment a transverse heat seal 172, uniting the walls of the flattened tubular sheath member 169, bars escape of the pad via one end of the sheath, while the other end may either be sealed shut, or, preferably, left as an open end 174 as shown. If end 174 is sealed shut, one may if desired provide an opening in another area of the sheath for pad removal, or provide a tear seal or other openable arrangement at end 174 or elsewhere in the sheath for the same purpose. In a preferred embodiment the tear seal or other openable arrangement will open in response to gentle shaking of the sheath when the pad is heavy from absorbed liquid. U.S. Pat. No. 3,683,919 discloses an openable sheath that is manually tearable longitudinally to discharge the sheath contents, and such an arrangement can be used in practicing the present invention. However, it is preferred to provide for discharge through an open or openable end of the sheath as described above, since such an arrangement is believed more likely to result in a smooth entry of the discharged material into the pool of water in the toilet bowl, thus reducing the incidence of splashing.

If desired, a substantially water impervious sheet may constitute, or be positioned against the surface of, that portion of the sheath which will be adjacent the back of the pad in use. The water impervious sheet may also extend from the back up along the sides of the pad for assisting in confinement of liquid. For example, an elongated strip of porous woven or non-woven fabric suitable for forming the sheath and a narrower elongated strip of water impervious material can both be advanced longitudinally in face to face contact with their center-lines coincident and may be sealed to one another followed by the steps, described in the preceding paragraph, of forming a tube and sealing to complete a sheath.

When the sheath is longer than the pad, the extra length at each end provides extensions 175 and 176 which are useful in securing the pad in the brief and in handling wet pads. For example, the extensions 175 and 176, respectively, can be used with elastic loops 26, 28 (FIGS. 2 and 3) to secure the pad 145 in place at the forward and rearward zones of the briefs 10. Also see the description of the use of the sheath under "Advantages" below.

It should be understood that all or any portion of the above optional pad concepts may be applied individually or in combination with one another. These individual and combined pad options may furthermore be employed with or without the above described brief.

The above-mentioned briefs assist in insuring a correct forward/rearward positioning of the pads. However, wearers who do not require such assistance can use a form of pad which needs no special briefs. For example, if the undersurfaces of the pads are coated with pressure-sensitive adhesive which is capable of tenaciously gripping fabric and which may be covered with a tear-away protective strip to be removed when the pads are ready for use, the pads can then be supported in conventional fabric underpants. Such embodiments preferably include the above-mentioned sheath having a water-impervious backing sheet.

For purposes of illustrating the method, the pad will include layers of highly absorbent material having between them a two-ply layer of tissue which performs a wicking action. FIGS. 16 through 40 illustrate the method of the present invention and suitable apparatus for carrying out said method on a continuous basis with the absorptive material and tissue being supplied in the form of strips wound into rolls.

The apparatus may include for example a tissue dispenser 200 and first and second absorptive strip material dispensers 220 and 240 positioned in sequence, with the tissue dispenser upstream of the absorptive strip material dispensers. Preferably each of the dispensers is provided with means for feeding strip material from either of two unwinding means whereby strip material may be dispensed from one of the unwinding means while a spent roll of strip material is replaced with a fresh roll on the other unwinding means. Appropriate placement of the unwinding means enables commencement of unwinding from the standby roll of strip material when the roll that is currently being unwound is exhausted.

Thus, the tissue and absorptive strip material dispensers of FIG. 16 are each provided with frames 201, 221 and 241, the upper unwinding means of which include first expandable mandrels 202, 222 and 242. These mandrels include means which can be selectively expanded or retracted to grip or release the core of a roll of tissue or absorptive strip material. Webs which unwind from the several rolls 203, 223 and 243 pass over guide rollers 204, 224 and 244 to tension sensing means. The webs pass respectively around sensor rollers 207A, 227A and 247A, pass diagonally across the respective tension sensor beams 205, 225 and 245 and around the remaining sensor rollers 207B, 227B and 247B. The respective tension sensor beams are biased around their respective pivots 206, 226 and 246 to pick up any slack which may develop in the webs, and are connected to linkages and brake mechanisms (not shown) which brake the respective mandrels 202, 222 and 242 sufficiently to inhibit development of slack in the webs and prevent over-running of the rolls 203, 223 and 243. Downstream of the respective tension sensing means are alignment rollers 208, 228 and 248 which direct the respective webs 209, 229 and 249 along the desired feeding paths.

Each of the dispensers 200, 220 and 240 includes a second unwinding means having components similar in nature and function to the first set of unwinding means described above. These include, respectively, second expandable mandrels 212, 232 and 252 for unwinding rolls 213, 233 and 253 around guide rollers 214, 234 and 254, across tension sensor beams 215, 235 and 255 provided with pivots 216, 236 and 256 as well as sensor rollers 217A, 217B; 237A, 237B; and 257A, 257B, and further around alignment rollers 218, 238 and 258 to guide the webs 219, 239 and 259 into the desired web feeding paths.

In operation, assuming that tissue is being fed from roll 203 on mandrel 202, a standby roll of tissue 213 is installed on mandrel 212. When roll 203 is exhausted, the feeding of roll 213 is commenced. The absorptive strip material may be fed from either of the upper mandrels 222 or 242 and from either of the lower mandrels 232 or 252. The unused mandrels in dispensers 220 and 240 are provided with standby rolls. When the upper absorptive material roll 223 or 243 is nearing exhaustion, feeding from the other upper roll is commenced. A similar routine is used to commence the feeding of the standby roll of absorptive material on one of the lower mandrels when the operational lower roll is exhausted. The depicted dispensers may of course be replaced with ones which have the capability of commencing the feeding of stand-by rolls on the fly.

According to a preferred embodiment the apparatus of the invention includes an aperture forming section shown in FIG. 17 including a cutter unit 270. The latter may for example have a frame 272 mounted on table 271 and comprising a base 273 upon which are erected two parallel plates, only one of which, plate 274, is visible in FIG. 17 in side elevation. The second parallel plate is directly behind the one shown and is spaced apart therefrom to provide space between them for mounting various processing rollers and cylinders, the latter having axles (not shown) journalled in bearings (not shown) mounted in the parallel plates. The axes of the respective rollers and cylinders are perpendicular to the plates, perpendicular to the direction of advancement of the material processed therein and parallel to the plane in which such material moves. The aperture forming section receives a composite comprising the strips of absorptive material separated by an intermediate layer of tissue, such composite being guided into the aperture forming section by an idler roller 276 mounted on frame extensions 275, one of which is visible in the drawing. The material then passes to top and bottom infeed drive rollers 277 and 278 from which it progresses to a cutting roller 279 having raised cutting projections to form the desired apertures, which projections bear against the top surfaces of, and pierce through, the composite, which is supported from beneath by a hardened plain cylinder 280.

As shown in greater detail in FIG. 18, constituting a fragmentary enlarged illustration of a portion of cutting roller 279 and the resultant material, the apertures or openings may optionally be formed in such a way as to cut through the material of the composite along a portion, but not all, of the perimeter of the respective openings, thereby forming in said composite hinge and flap members. As shown in FIG. 18 and in an enlarged portion of FIG. 18 shown in FIG. 18A, the peripheral surface of cutting roller 279 is provided with a regular pattern of cutting dies 281 having their cutting edges arranged in a configuration which will cut the absorptive layer material(s) along lines that partly but not completely surround the area of the intended openings 134. A first portion 282 of the perimeter of each opening is cut, and a second portion 283 of the perimeter is not cut. These uncut portions 283 form hinge members, while the cut portions define not only portions of the openings, but also the perimeters of flap members 284.

While FIG. 18A represents the outline for the cutting edges of dies 281 on cutter roller 279, it also represents the cutting line formed in the work material. As the figure indicates, the die and its corresponding cutting lines include gentle, smooth curves 285 which respectively form and curve past the edges of the hinge portions to ends 286 which diverge from one another. This can assist in inhibiting tear propagation in the layer(s) in and/or adjacent the hinge members. In this embodiment the gently, smoothly curved portions of the dies and cutting lines also include curved transitions 287 from the openings per se to positions alongside the hinge portions.

When hinge and flap members are formed, the flap members should be displaced, in one or more steps, so that they do not block the openings from they are formed when the composite is formed into pad stock. Coincident hinge and flap type openings in the several layers of a moving composite, if displaced outwardly together, can cooperate to bind the layers together and promote coordinated movement of the several layers. Best results are attained when the hinges are formed with lesser width, measured along the hinge bending lines, than the maximum widths of the openings, measured parallel to said bending lines, and the hinge members are formed by cutting lines which curve in the above-described manner. The above-mentioned displacement of flap members may be accomplished in one or more steps.

As shown in FIGS. 17 and 19, this is preferably accomplished in two steps employing a knock-out roller 289 driven in synchronization with cutting roller 279 and having spikes 292 or other projections positioned so that they will contact the composite 293 passing from roller/cylinder combination 279/280 in registry with the respective flap members 284 and displace said flap members outwardly, in this case downwardly, relative to the composite and openings 134. The displaced flaps temporarily enter small pits 294 in a pocket roller 290 which is mated to knock-out roller 289 as shown in FIG. 19.

In an optional second displacement step shown in FIG. 20, the composite 293 and the flap members 284 are rolled between flattening cylinders 299 and 300 whereby the flap members are displaced inward, in this case upward, relative to the composite. Thus the flap members can be flattened against portions of the composite adjacent the respective hinges 295 while leaving the respective openings 134 substantially open, i.e. not blocked by the flap members. When the previously described first displacement (and second displacement, if any) are performed in such a manner that the flaps 284 are left extending away from the composite 293 from which they are formed, and the layer or layers are eventually formed into an undulating pattern which is retained in the resulting pad, these flaps can act as spacers between adjacent undulations for promoting a high absorption rate. After the displacement operation(s), as shown in FIG. 17, the apertured composite 308 then passes over outfeed idler roller 304, rotatably mounted on fixed downstream frame extension 303, and traverses the idler roller 307 of constant tension device 305 having a horizontal arm 306 which translates roller 307 upwardly and downwardly to maintain constant tension in web 308.

As shown in FIG. 21 the preferred apparatus for performing the method of the present invention includes a pad stock folding section 321 and an absorbent fiber wrapping section 430, these elements being mounted in a common frame 315 having longitudinal stringers 316, uprights 317, transverse members 318 and a frame extension 319. The apertured web 308 from the cutter unit 270 passes over infeed idler roller 320 rotatably mounted in the frame extension 319 and immediately passes into folder 321. The latter includes frame members 324 supported by first and second legs 322, 323. Within frame 324 are distributed a first array of upwardly directed rails 325 in the lower portion of frame 324 beneath web 308. A second array of downwardly directed rails 326 is positioned in the upper portion of frame 324 above web 308. The rounded infeed ends 327 of arrays 325 and 326 facilitate entry of the web with dependent flap members 284 as shown in FIG. 20.

Rails 325 in the lower array extend in the general direction in which the web moves but, as shown in FIGS. 22-24, are spaced laterally from one another. The rails 326 extend in the same longitudinal direction and are also laterally spaced from one another with the rails 326 being positioned above or within the space between the rails 325. For simplicity, the longitudinal convergence of rails 325 and 326 has been eliminated from the background in FIGS. 22-24. Scanning the respective arrays from left to right in cross section, it will be seen that the upper and lower rails 326 and 325 alternate laterally across the structure. While the upper surfaces 330 of rails 325 are all in a common plane and the lower surfaces 331 of rails 326 are also in a common plane, these planes are not parallel. Thus there is a small vertical spacing between said planes at the infeed end of folder 321. These planes intersect with one another intermediate the infeed ends 327 and output ends 328 so that the lower surfaces 331 of rails 326 are below the upper surfaces 330 of rails 325 at their output ends. Also, as the rails extend from their infeed ends downstream towards their output ends 328 they converge laterally. By virtue of the intersection of the above mentioned planes and the lateral convergence of the two arrays of rails, the advancement of web 308 and dependent flaps 284 longitudinally through the folder causes a plurality of bends 329 to form in the web running lengthwise thereof and spaced at intervals across the width of the web between flaps 284. In such manner the web 308 is formed into an elongated pad stock which is of greater thickness and narrower width, in which the web has a zig-zag configuration and in which the flaps can act as spacers between the undulations of the zig-zag pattern.

Referring again to FIG. 21, the pad stock comprising folded web 308 is drawn out of the folder section 321 by a rotating disc-cylinder assembly adjacent the output ends 328 of the rails 325 and 326. This assembly comprises stanchions 340, which are visible in FIGS. 21 and 25, and between which is secured a driven, rotating array of discs 341 in which the respective discs are mounted with their apexes at substantially the same elevation as the output ends 328 of the upwardly directed or lower rails 325, the discs also being spaced apart laterally by the same distances as, and also aligned with, the corresponding output ends 328 of these rails. An elastomer-surfaced cylinder 342 positioned above disc array 341 maintains contact with the upper outer surfaces of the upper bends in the pad stock, and urges the inner surfaces of such bends into driving contact with the edges of the respective discs in array 341. The pressure of cylinder 342 against the bends in the pad stock and the disc array 341 can be set with adjusting screw 343 and handle 344.

Figure 25:
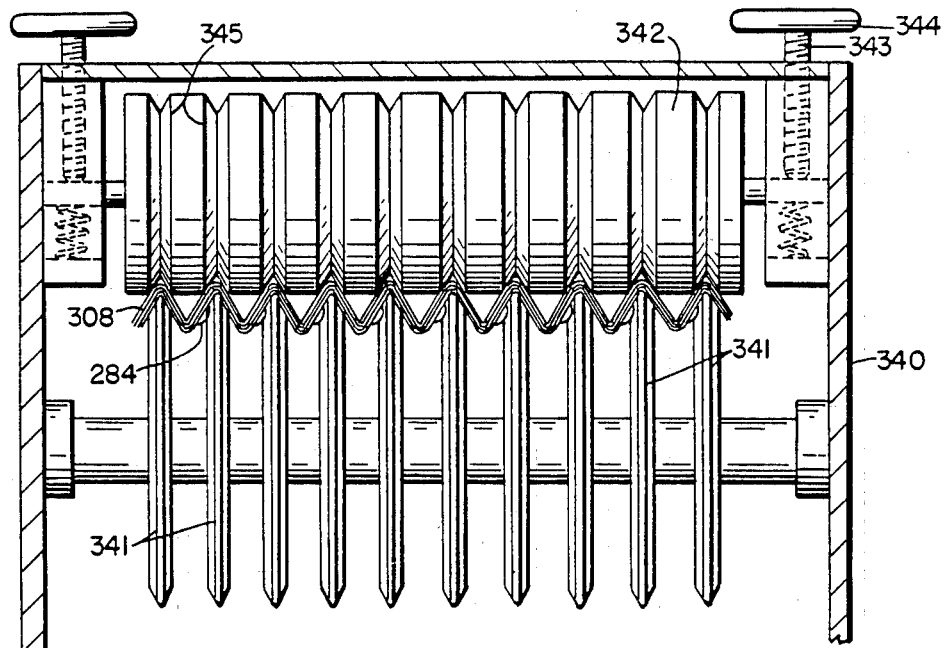
FIG. 25 is a sectional view taken along section line 25—25 in FIG. 21, showing a rotating disc array and cooperating grooved cylinder for assisting in drawing the strip of absorptive material through the bending section of FIGS. 21-24.

As shown in part in FIG. 25 and in greater detail in FIG. 25A, an enlarged portion of FIG. 25, it is recommended that elastomer-surfaced cylinder 342 be provided with grooves 345 in alignment with discs 341. FIG. 25A shows that the peripheries 346 of the discs include champhered or convergent surfaces 347 which intersect in curved surfaces or radii 348, as viewed in a plane which includes the axes of rotation of the discs. These radii inhibit cutting of the web 308 at the extreme upper portions of the bends 329 which are compressed between and frictionally engaged by the convergent disc peripheral surfaces 347 and the groove walls 345. This grooved arrangement has proven to be of significant assistance in controlling machine gain relative to the travelling web 308 at the downstream end of the folding section 321 of FIGS. 21-24. The appropriate amount of traction between discs 341 and webs 308 with varying stiffness and frictional characteristics can be obtained by varying the included angle and depth of grooves 345.

In a preferred embodiment of the method and apparatus for carrying out the invention, a second disc-grooved cylinder assembly (not shown) is provided wherein the discs are located above the folded web 308 to force the lower outer surfaces of the bends into contact with the grooves in the cylinder. This disc-grooved cylinder assembly, which is inverted from that shown in FIG. 25, may be positioned either upstream or downstream of the FIG. 25 assembly, each assembly being adjusted so that the discs of each assembly are aligned with the apexes of the inner surfaces of the bends in the folded web 308. These disc-grooved cylinder assemblies serve not only to draw the folded web out of the folder section 321, but also to crease the material at the folds sufficiently so that the folded configuration is maintained and the height and width of the folded webs are established.

Figure 26:
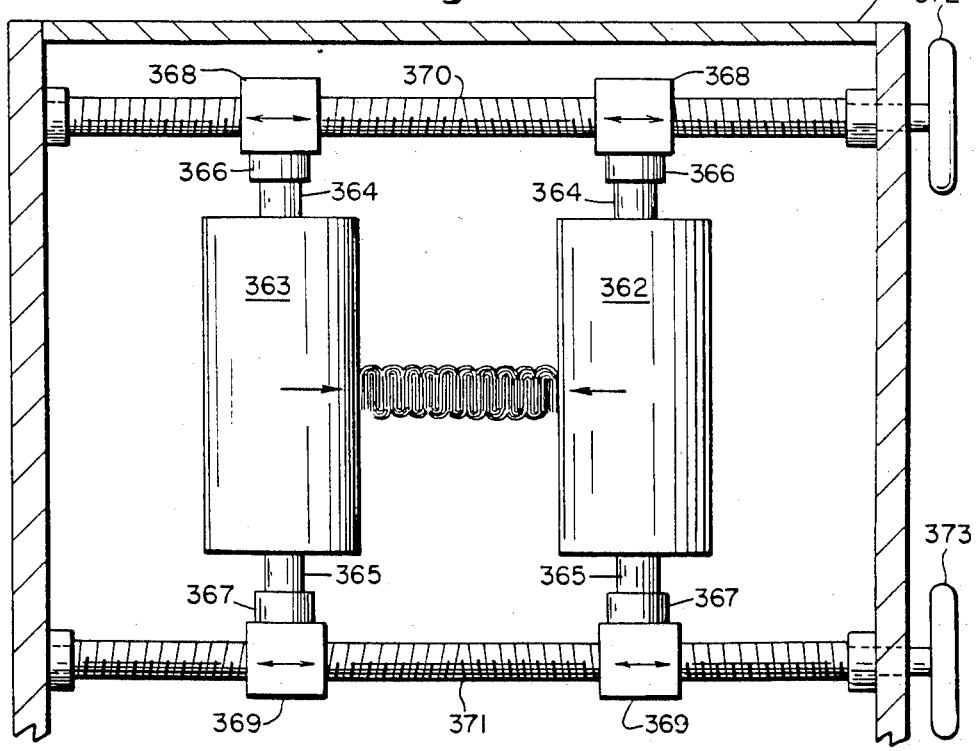
FIG. 26 is a sectional view taken along section line 26—26 in FIG. 21 showing confining means which receive the layers of absorptive material in zig-zag configuration from the bending section.

Apparatus that includes only one disc-grooved cylinder assembly preferably is provided with means to control the width of the pad stock as is shown, for example, in FIGS. 21 and 26. As shown in these Figures, the width and lateral position of the pad stock can be controlled by lateral support means 360 comprising sub-frame 361 mounted on the frame 315 and supporting a first roller 362 and a second roller 363. These rollers are downstream of disc arrays 341 and cylinder 342 and are mounted with their axes vertical so that they laterally confine or compress the pad stock between them.

These rollers may be mounted in such a way as to provide for adjustment of their lateral spacing. For example, the shaft means 364, 365 supporting the rollers 362, 363 in a vertical position may be rotatably mounted in bearings 366, 367 secured to blocks 368, 369 which are laterally shiftable in subframe 361. The upper and lower blocks, indirectly supporting both ends of the left and right rollers, are each threadedly engaged with one of two oppositely pitched thread sections on adjusting screws 370 and 371 having handles 372 and 373. Thus, adjustment of screws 370, 371 controls the lateral gap between rollers 362, 363.

After the above mentioned pad stock has been formed, it is advanced longitudinally and brought into contact with at least one strip of liquid permeable material such as absorbent fiber material which is wider than the pad stock. The pad stock and fiber material strip are then caused to advance together longitudinally while bending the strip along longitudinal lines for encircling the pad stock, as viewed in transverse cross section. Thus a wrap of fiber material is formed around the pad stock. As shown in FIG. 21, this may be accomplished with the aid of fiber material dispenser 380, 390 and 400 operating in combination with folder 321 and a wrapping section 430. These dispensers are similar to the dispensers 200, 220 and 240 of FIG. 16, except that they each include only one unwinding means. Thus the respective dispensers 380, 390 and 400 include frame members 381, 391 and 401 and expandable mandrels 382, 392, and 402 which support rolls 383, 393 and 403 of fiber material for rotation and unwinding. As the fiber material unwinds it passes over guide rollers 384, 394 and 404 to the sensor rollers 387A,387B; 397A,397B and 407A,407B of tension sensor beams 385, 395 and 405 having pivots 386, 396 and 406 which function in the manner described above. From these are delivered fiber webs 389, 399 and 409 which pass over guide rollers 388 and 408 along the desired feeding paths.

After passing guide rollers 388 and 408, the fiber wrap webs enter a gap 412 situated between first and second pinch point rollers 410, 411. The webs then pass to fiber material infeed rollers 414, 415 mounted on subframe 413 and adjustable by means of compression adjustment screw 416 and handle 417.

In the preferred mode of operation, any two of the mandrels 382, 392 and 402 are employed to unwind two operational rolls of two ply fiber material. Thus a pair of webs, drawn from any two of the three mandrels, is caused to pass between pinch point rollers 410, 411 to the infeed rollers 414, 415 and from thence into contact with the underside of the pad stock. While two of the mandrels are unwinding operational rolls, the third mandrel may be loaded with a standby roll. When one of the operational rolls has run out, the unwinding of the standby roll may be commenced.

The pad stock and the wider underlying double layer of the fiber material enter wrapping section 430 with the aid of pad stock and fiber material belt feeders, such as upper feeder 431 and a longer lower feeder 432. The upper feeder includes a belt 433 held in position by upper infeed belt roller 435 and upper outfeed belt roller 436 so that the lower driving surface of belt 433 contacts the upper surface of the pad stock. The belt 434 is held in position by lower infeed belt roller 437 and lower outfeed belt roller 438 with the upper driving surface of belt 434 in contact with the underside of the fiber webs. The belt feeders 431, 432 are driven so as to transport the pad stock and fiber webs from left to right towards the channel 439 which is secured to the frame of lower belt feeder 432 and is further supported at its downstream portion 446 by a channel frame member 440. Upper belt feeder 431 terminates a short distance upstream of channel 439 while the longer belt feeder 432 extends beyond the downstream end of channel 439 with its belt 434 inside channel 439 along its inner surface 441. See the detailed cross sectional views of FIGS. 27, 28 and 29, in which the channel 439 has upturned side walls 442 which converge laterally and progressively increase in height in the downstream direction, thereby diminishing the width of the channel inner surface 441 and causing the marginal edges 447 of the fiber material to turn upward as the fiber material passes through the longitudinal mid-portion 443 of the channel. As the side walls 442 converge still further, approaching channel downstream portion 446 (FIGS. 21 and 29), they are bent inward more or less horizontally to form top walls 446 extending into downstream portion 446 and causing the marginal edges 447 of the fiber material to overlap one another. This causes the fiber material to fully enclose or encircle the pad stock as viewed in transverse cross section, thereby forming a wrap of fiber material around the pad stock.

According to one embodiment of the invention the pad stock and fabric wrap are cut transversely in a common cutting step to form pads of predetermined length therefrom. According to the present embodiment of the invention, as shown in FIGS. 30, 31 and 31A, such cutting can be accomplished while the pad stock and fiber web are advancing longitudinally, pads of predetermined length being cut therefrom. As indicated in FIG. 30, this may be accomplished for example by pad cutting section 460 erected on table 461 and having a frame 462 of parallel plates 464 mounted on base 463. The plates 464, only one of which is visible in side elevation in FIG. 30, are aligned generally parallel to the direction of material flow and are spaced apart a sufficient distance for the passage of processed material and for the mounting of a cutting roller and corresponding cylinder between the plates. An upstream frame extension 465 supports belt feeders 466 and 467 which receive the wrapped pad stock from wrapping section 430 in FIGS. 21 and 29. The surface of the wrapped pad stock is contacted by the upper surface of lower belt 468, supported, driven and tensioned by lower infeed roller 469, lower outfeed roller 470 and tension roller 471 in lower belt feeder 466. The upper surface of the wrapped pad stock is engaged by the lower drive surface of upper belt 472, supported, driven and tensioned by upper infeed roller 473, upper outfeed roller 474 and tension roller 475 in upper belt feeder 467. Belt feeders 466 and 467, driving in unison, deliver the wrapped pad stock to the nip 476 of a raised edge cutting roller 477 having raised cutting edges distributed at angularly spaced intervals about its periphery, the peripheral distance between such cutting edges corresponding with the desired pad length.

As shown in the enlarged views of FIGS. 31 and 31A, the cutting edges 481 are situated at an appropriate radial distance from the center of rotation of roller 477 so that they bear against the smooth surface of a polished hardened steel plain cylinder 478 which supports the raised pad stock during cutting while rotating in unison with, i.e. at the same peripheral speed as, cutting roller 477. The cutting pressure exerted by cutting roller 477 can be adjusted by means of compression adjusting screw 479 with handle 480. Preferably, cutting edges 481 include generally upright but downwardly convergent forward and rearward surfaces 482 and 483 which both intersect with a narrow compression surface 484 that is inclined downwardly in the direction of movement of the work through the rollers 477, 478 and is more nearly horizontal than vertical. The intersection of surfaces 482 and 484 forms a cutting edge and the surface 484 applies compression to a narrow band of material 485 adjacent the trailing edge of each cut. This causes collapsed and overlapping undulations and/or other layers in the pad stock to cling to one another with sufficient adherence to form a coherent leading edge 487 at the front of each pad 486 which retains substantial structural integrity during subsequent advancement of the resultant cut pad sections. When the cut sections are advanced longitudinally into contact with sheath material while the latter is advancing longitudinally at an accelerated rate, these coherent leading edges help resist fraying of the pads 486 and/or jamming of the equipment.

It should be understood that the lengths of wrapped pad stock can themselves function as absorbent pads. However, for reasons explained above it is useful to provide such pads with an outer sheath, such as for instance a sheath material which is permeable to the liquid to be absorbed and yet retains its structural integrity when moistened with the liquid. This sheath can perform optional but useful protective and/or handling functions described above. Such protective functions include, for example, inhibiting the wicking of moisture from a wet pad within the sheath to the outer surface of the sheath which would likely be in contact with the wearer's skin in the case of an incontinence care pad. The handling functions include providing a length of material extending generally longitudinally from each end of the pad for use in securing the pad within a garment and/or carrying the used pad from the garment to a disposal point such as a toilet. Depending on whether protective and/or handling functions are needed in respect to a particular absorbent pad product it may or may not be desirable to apply a sheath member to the pads. If such sheath member is applied it may or may not be desirable to provide a significant increment of additional length in the sleeve, as compared to the length of the pad, to facilitate handling. The formation of a sheath with or without extensions of substantial length can be performed by the remaining portions of the machine shown in FIGS. 32 through 39 and comprising a sheath material application section, a sheath material longitudinal sealing section and a cutting section to be described in greater detail below.

Figure 32:
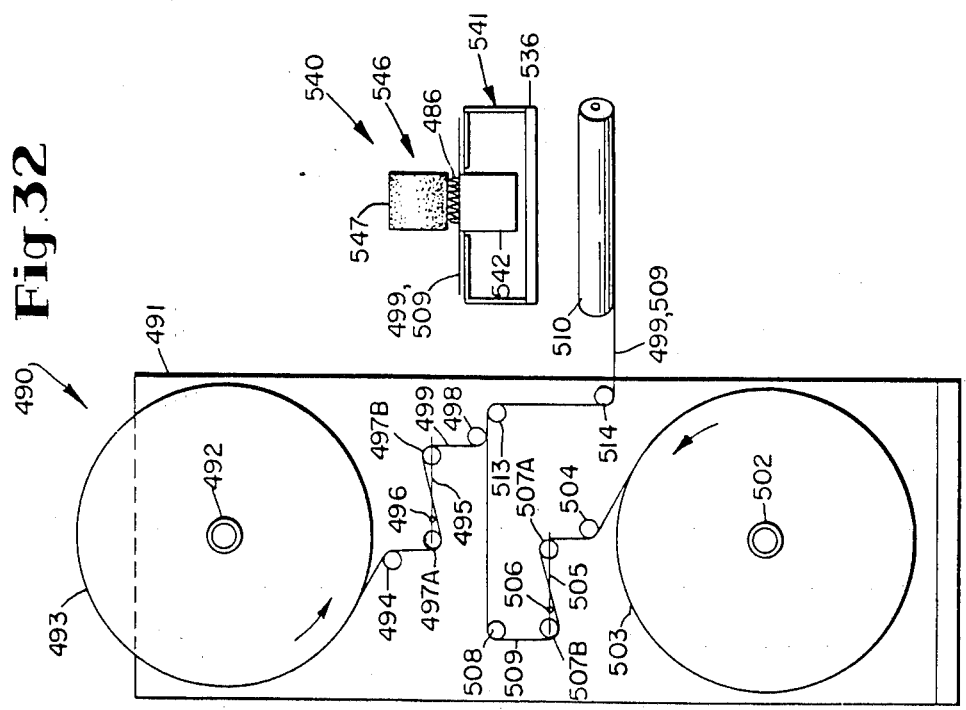
FIG. 32 is a sectional view taken along section line 32—32 in FIG. 30, illustrating a sheath material dispenser which feeds sheath material in strip form to a translation roller in the sheath material application section of FIG. 30.

The sheath material application section, shown in FIG. 32, includes a sheath material dispenser 490 similar to the tissue dispenser 200 of FIG. 16. It is mounted to one side of the material flow path through the main portion of the apparatus, with its frame 491 perpendicular, and its mandrels 492, 502 parallel, to the direction of travel of material through said flow path. Thus, as in the previously described dispenser, the mandrels 492 and 502 support standby and operational rolls 493 and 503, but in this case the rolls are rolls of the sheath material. The latter passes around guide roller 494 or 504 to the sensor rollers 497A,497B; 507A,507B of the tension sensor beams 495, 505 with pivots 496, 506 and from thence to alignment rollers 498, 508 which direct the webs 499, 509 of sleeve material via further guide rollers 513 and 514 to the underside of a translation roller 510 (FIGS. 30 and 32) supported by stanchions 511 and 512 on table 461 (not shown in FIG. 32). Translation roller 510 is mounted with its rotational axis in a horizontal plane and at an angle of 45° to the direction of travel of the pad stock and wrapped pads. Sheath material passes from dispenser 490 in a direction perpendicular to the main material flow path and in the process of passing around translation roller 510 is redirected so that as it leaves the top of roller 510 it then moves in a direction directly opposite to the flow of wrapped pads but at a lower elevation than the pads. As best shown in FIG. 30, after the web of sheath material 499,509 is turned upstream by roller 510, it passes around a turning roller 521 mounted in frame extensions 520 secured to the parallel plates 464 of pad cutting section 460. From roller 521 the material progresses to the nip of first and second sheath material infeed rollers 522,523 driven at the same peripheral speed. The compression between rollers 522 and 523 may be adjusted by compression adjustment screw 524 with handle 525. The infeed rollers draw the web from translation roller 510 and deliver it to a turning and alignment roller 526 journalled in bearings (not shown) mounted in the parallel plates 464. As the web clears roller 526 it is at the appropriate elevation to receive the cut-to-length pads discharged from cutting roller 477 and cylinder 478, thus becoming a support for the pads as they travel further downstream in the process.

Depending on how long one wishes to make the sheath, as compared to the pad length, thereby controlling the length of the sheath extensions, the web of sheath material will be caused to travel at a somewhat greater velocity than the velocity of the pads ejected by cutting roller 477 and cylinder 478. The greater speed of the sheath material web causes the pads to advance longitudinally at an accelerated rate relative to the rate of advancement of the pad stock and outer wrap during cutting, thereby causing the pads to travel longitudinally on the sheath material web with a predetermined space therebetween. By adjusting the difference in said rates one can adjust the lengths of the sheath extensions to be formed subsequently, such lengths varying for example from the minimum distance required to seal the sheath material at one or both ends of the pad, to the maximum useful length of sheath extension which might be employed for securing the sheaths and pads in a garment and/or transporting them from the garment to a disposal receptacle. According to one embodiment the pads are caused to travel longitudinally on the sheath material with a predetermined space between the pads which is about twice the combined length of the sheath extensions which are to be formed. The advancement of the pads and sheath material web is assisted in part by upper and lower pad/sheath material drive rollers 528/529 mounted for rotation in second frame extensions 527 secured to parallel plates 464 of the pad cutting section 460. The pressure developed between rollers 528 and 529 may be regulated by compression adjusting screw 530 with handle 531.

According to an optional embodiment of the invention the sheath material is bent along a longitudinal line or lines for encircling the pads. In the present preferred embodiment such bending is accomplished while the pads are being carried upon and advanced longitudinally with the sheath material. As shown in FIG. 30, the preferred apparatus for performing this operation is mounted on a sheath material wrap and seal sub-frame 533 including lower stringer 534, uprights 535 and upper stringer 536 upon which is mounted the feeder/sheath wrapper section 540.

As may be seen in FIG. 30 and in FIG. 32, from which the equipment supports and background detail have been omitted, the cut-to-length pads supported on the wider underlying layer of sheath material enters sheath material application section 540 with the aid of pad and sheath material belt feeders, such as upper feeder 546 and a longer lower feeder 541. The upper feeder 546 includes a belt 547 positioned, driven and tensioned by upper infeed roller 548, upper outfeed roller 549 and tension roller 550, so that the lower driving surface of belt 547 contacts the upper surfaces of the pads 486. The belt 542 is positioned, driven and tensioned by lower infeed roller 543, lower outfeed roller 544 and tension roller 545 with the upper driving surface of belt 542 in contact with the underside of the sheath material 499,509. The belt feeders 541, 546 are driven so as to transport the pads and sheath material from left to right (as viewed in FIG. 30) towards the channel 551 which is secured to the frame of lower belt feeder 541 and is further supported at its downstream portion by a frame member 552. This channel assists in wrapping the sheath material about the pads.

Figure 33:
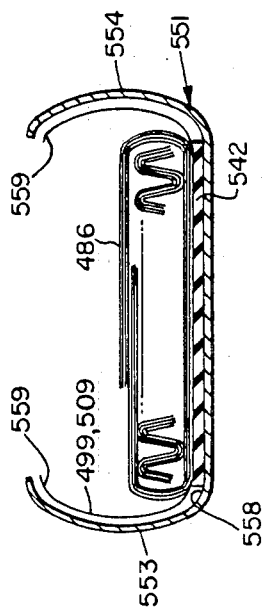
FIG. 33 is a sectional view taken along section line 33—33 in FIG. 30, disclosing a stage in bending of the sheath material to encircle the wrapped pads which are being carried on the sheath material through the sheath material application section of FIG. 30.
Figure 34:
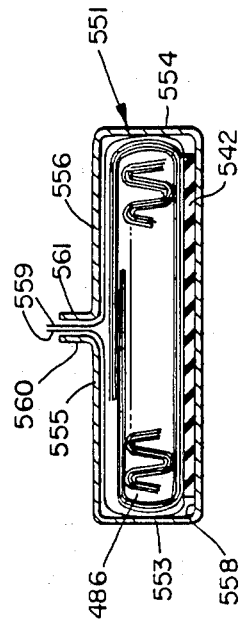
FIG. 34 is a sectional view taken along section line 34—34 in FIG. 30, showing completion of the bending depicted in FIG. 33.

Referring now to FIG. 30 and cross-sectional views 33 and 34, the shorter upper belt feeder 546 terminates a short distance upstream of channel 551, while the longer, lower belt feeder 541 extends beyond the downstream end of channel 551 and belt 542 extends inside channel 551 along its inner surface. As shown in FIG. 33 channel 551 has left and right lateral fences 553, 554. These converge laterally in the downstream direction, thereby diminishing the width of the channel floor 558 and causing the marginal edges 559 of the sheath material 499,509 to turn upward as it passes through the longitudinal mid-portion of channel 551 as shown in FIG. 33. As the upper edges of these fences approach the channel downstream portion which is shown in cross-section in FIG. 34, they are lengthened and bent to a horizontal configuration to form left and right inward projections 555,556, with upturned lips 560,561 at their inner extremities. These cause the marginal edges 559 of the sleeve material to project outwardly relative to the nearest major surface of the pad stock or pads 486, in this case turning generally upwardly, while also enclosing or encircling the pads as viewed in transverse cross section, thereby forming a wrap of sleeve material around the pads.

Figure 35:
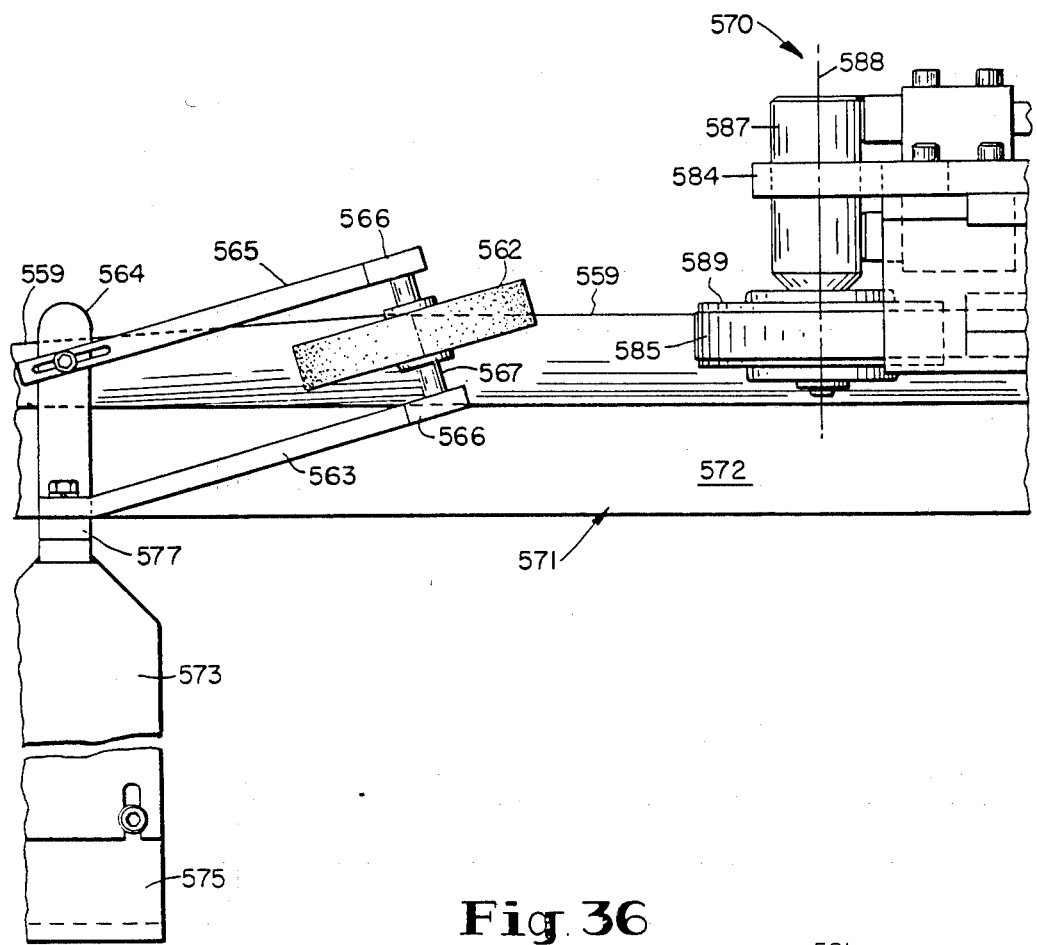
FIG. 35 is an enlarged portion of FIG. 30 showing inclined rollers for presenting the marginal edges of the sleeve material in an outward direction relative to the wrapped pad stock and feeding such edges into the belt-type fusion bonding apparatus of FIGS. 30 and 36.

As shown in FIG. 30, and in greater detail in its enlarged portion illustrated in FIG. 35, the outward projection of the longitudinally advancing marginal edges can be assisted or caused to occur by advancing said edges through the nip of a pair of abutting, driven or non-driven rotatable rollers having their axes of rotation inclined from the vertical in the upstream direction. If the pad stock is travelling generally horizontally with the sheath material marginal edges above it, and projecting upwardly, and with the inclined axis rollers being situated above the pad stock, such rollers will cause lifting of the marginal edges and are preferably employed to feed the marginal edges from channel 551 into sealer section 570. In the present embodiment, the rollers 562 (only one of which is visible in FIGS. 30 and 35) are supported by the same base 575, stanchion 573 and transverse member 577 that support the sealer section 570, to be described in greater detail below. The second roller abuts with and is directly behind the one shown, on the opposite side of the work. The two rollers have left and right-hand mounting brackets of similar design, including lower support arms 563 and posts 564 secured to transverse member 577, as well as upper support arms 565 secured to posts 564. Support arms 563 and 565 have a moderate upward inclination in the downstream direction and have at their downstream extremities bearings 566 rotatably supporting the shaft 567 with its axis of rotation inclined in the above-described manner. The rollers 562 are rotated on these shafts by the work which frictionally engages the rollers as it passes between them. Thus, the sheath material lateral edges 559, presented upwardly upon discharge from channel 551, rise from left to right as they progress from channel 551 toward the rollers 562. The inclined rollers discharge the sheath material 499,509 with the pads 486 within (not shown) and with the marginal edges 559 at the proper elevation for bonding, to the sealer section 570. Adjusting means can be provided to vary the inclination, and therefore the lifting tendency, of the inclined axis rollers.

Figure 40:
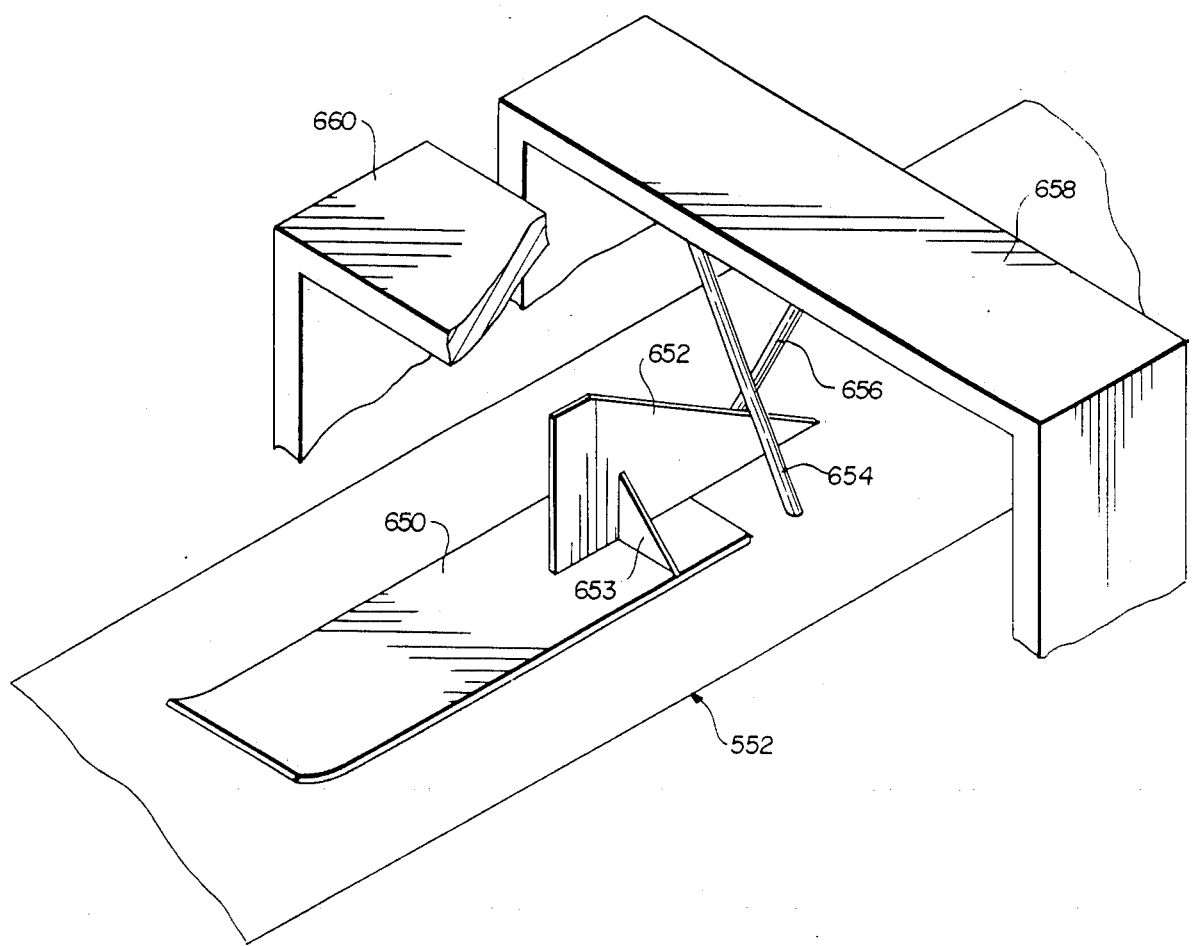
FIG. 40 is a perspective view of an alternative embodiment of a stage for enclosing pads in sheath material.

In an alternative embodiment, which is currently being used, sheath material is wrapped around the pads without the use of channel 551 to cause the marginal edges 559 of the sheath material 499, 509 to turn upward and inward to enclose the pads. In this alternative embodiment, advantage is taken of the tendency of each portion of sheath material, in a continuous length of sheet material, to conform to adjacent portions. Thus, when a leading end of sheath material has been forced into a configuration enclosing the pad, the following sheath material as it moves downstream, is gradually urged into the conformation enclosing the pads. As shown in FIG. 40, hold-down plate 650 is supported above lower belt 542 by frame 660, (only a portion of which is shown), fin 652, and web 653. As sheath material is advanced by lower belt 552 toward rollers 562 the marginal edges 559 are advances towards rollers 562 the marginal edges 559 are pulled upward and inward by the rollers 562. Intermediate the ends of hold-down plate 650 and rollers 562 are metal fingers 654, 656 held in place above metal hold-down plate 650 by frame 658. These fingers are each disposed at about a 45° angle to the hold-down plate and together with fin 652, serve to guide the marginal edges 559 of sheath material 599, 509 into engagement with the nip of rollers 562.

Figure 36:
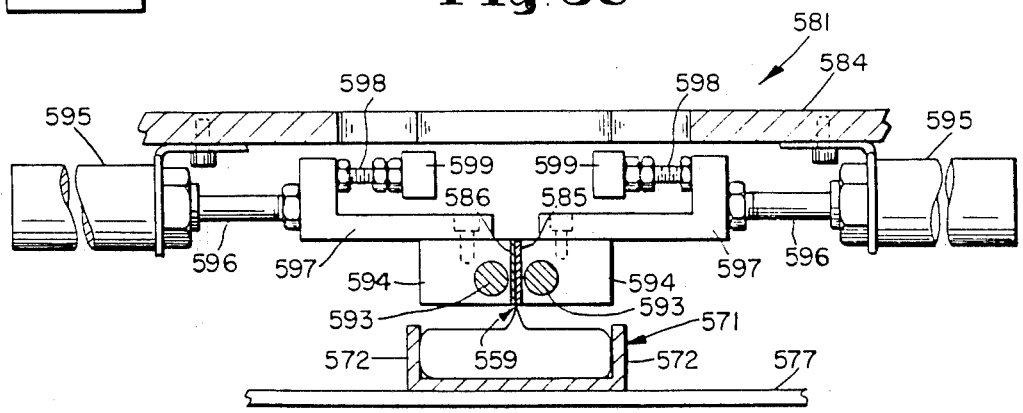
FIG. 36 is a partial sectional view, partially schematic, taken along section line 36—36 in FIG. 30, showing details of the sheath material longitudinal heat-sealing apparatus.

The next optional but preferred step is the fusion bonding of the open mesh sleeve material surrounding the pads for forming sleeve stock. As shown in FIGS. 30, 35 and 36, this step is preferably performed continuously employing heated, abutting, rotating metal belts while the pads are advanced longitudinally and with the sheath material surrounding them to form continuous running length sleeve stock surrounding the pads. When the pads and sheath material, thus configured, are received into sealer section 570, they slide through a longitudinally positioned tray 571 having sides 572 for confining the work material against lateral motion. The tray 571, which is supported upon transverse members 577, 578 held up by stanchions 573, 574 and connected by bases 575, 576 to subframe 533, also extends beneath the inclined axis rollers 562 and thus in certain circumstances may assist in holding the work in the desired orientation and at the appropriate elevation in alignment with the plane of abutment of the cooperating sealing belts.

The sealing belts are mounted in subframe 581, including first and second upright standards 582, 583 that support an overhead horizontal plate 584. Mounted in apertures in this plate are the various supports for the sealing belts which are positioned adjacent one another so as to squeeze the sheath material marginal edges 559 between them to cause said edges to fusion bond to one another and to draw the sheath material downstream by coordinated movement of the belts, i.e. at the same peripheral speed.

As shown in the drawings, there are right and left sealing belts 585,586 having infeed idler units 587 in which there are vertical axles (not shown) on center lines 588 which support infeed belt rollers 589 at the appropriate elevation. The opposite ends of the sealing belts are supported by outfeed drive units 590 with vertical axles 591 supporting outfeed belt rollers 592. Resistance heaters 593 provided with suitable temperature control means (not shown) supply heat to heat transmission blocks 594 which frictionally engage the back sides of the the moving sealing belts 585,586 to maintain them at the proper temperature for sealing the sheath material. As shown in FIG. 36, the sealing pressure of belts 585,586 against the marginal edges 559 as well as the pressure of heat blocks 594 against the belts is maintained by a pair of pneumatic cylinders 595 underslung on plate 584 and having rams 596 and ram extensions 597 which can reciprocate perpendicular to the sealing axis of the belts and which support the blocks 594. The maximum inward projection of the blocks 594 and the above-mentioned pressures are governed by abutting contact between ram extensions 597 and a pair of adjustable stops 598 secured to fixed frame members 599.

It has been found possible to fusion bond the material surrounding the pads with the apparatus configured as shown in the drawings but with the metal belts 585, 586 omitted. The sheath material marginal edges 559 are bonded by radiating heat into them from heat transmission blocks 594 and then pressing the heated surfaces together with rollers 592 to fuse them. Blocks 594 are positioned about 3 mm from the surfaces of marginal edges 559.

The resultant sleeve stock with pads within, received from sealer section 570, may be sealed transversely at one or both ends of the pads and cut to an appropriate length. For example, if the sleeve stock is sealed transversely, this can be done while the sleeve stock and pads are advancing longitudinally. Cutting may also be performed at longitudinal positions intermediate the pads with the pads and sleeve stock in longitudinal motion, thereby forming absorbent pads within sheaths having sheath extensions extending a predetermined distance beyond the ends of the pads, the sheath material being sealed at neither, one or both ends of the pads. The foregoing maybe accomplished for example, by the sheath sealing and cutting section 600 of the preferred apparatus illustrated in FIGS. 37-39.

Section 600 includes a table 601 supporting a base 602 on which are mounted generally upright parallel plates 603 extending parallel to and on each side of the flow path of the continuous running length sleeve stock having spaced pads inside. An upstream frame extension 604 supporting a belt feeder 605 assists in moving the sleeve stock from sealer section 570 into this section of the apparatus. The belt feeder includes a lower belt 606 having its upper driving surface in contact with the bottom of the sleeve stock, the belt 606 being supported, driven and tensioned by lower infeed roller 607, lower outfeed roller 608 and tension roller 609. Upper infeed roller 611, upper outfeed roller 612 and upper tension roller 613 support, drive and tension the upper belt 610 with its lower driving surface in contact with the upper surface of the sleeve stock. Operation of belts 606 and 610 in unison feeds the sleeve stock at the same longitudinal rate of advancement at which it is discharged by the sealing belts 585 and 586 of sealer section 570. Belt feeder 605 delivers the sleeve stock to the nip 614 of sealing roller 615 with transverse sealing bar 636 and cooperating hardened polished plain cylinder 616 shown in greater detail in FIG. 38. Sealing pressure can be applied and regulated with the aid of hydraulic cylinder 617 mounted in upper frame extension 618 and having its ram 619 pivotally connected to toggle 620 which vertically adjusts compression link 621, thereby exerting more or less sealing pressure on roller 615 through its shaft and bearings (not shown). There is a pair of the above-described combinations of hydraulic cylinder, frame extension, ram, toggle and compression link, one at each end of the shaft of bar seal roller 615, but only one such combination is visible in the drawings.

The cutting operation may be performed with a raised edge cutting roller 622 which is shown in FIG. 37 and in greater detail in FIG. 39, having its raised transverse cutting edges 629 spaced about the periphery of roller 622 at distance intervals equal to the desired sheath length. A cooperating lower cylinder 623 is provided, similar to cylinder 478 of FIG. 30. Cutting pressure is applied and adjusted by hydraulic cylinder 624 on frame extension 625 with ram 626, toggle 627 and compression link 628 cooperating with corresponding components connected to the other end of the shaft (not shown) on which cutting roller 622 is mounted. The completed absorbent pads within sheaths having sheath extensions extending a predetermined distance beyond the ends of the pads are discharged from cutting roller 622 and lower cylinder 623 onto a discharge conveyor 630 having a belt 635 supported by infeed and outfeed rollers 633,634 mounted in subframe 631 with frame extension 632, the latter being supported on the same table 601 which supports the sleeve sealing and cutting section 600.

Best Mode

At present it is considered best to form the brief as described in connection with FIGS. 1-4, above. The oval impervious laminated panel 18 is heat-sealed to the inside of the crotch portion of the briefs by an essentially continuous oval heat-seal positioned about 1.3 cm inwardly of, and all the way around the peripheral edge of panel 18, the side portions of which edge overlap the elastic leg bands of the briefs. With the briefs folded flat so that the fabric is folded at the sides of the elastic waistband and across the lowest point in the crotch, the front of panel 18 will be about 10 cm above the rear of said panel in a typically sized brief.

For best results, it is considered advisable to form the pad from a composite of tissue and absorptive layers including swellable polymers, preferably particulate starch graft polymers, such as the Sanyo material sold under the trade designation Sap-sheet 4000-S(W), and/or Dow water absorbent polymer films, such as that contained in the laminates sold under the trade designations DWAL 30R, DWAL 30F, DWAL 35R and DWAL 35F, the perforated flexible grades being preferred. The Dow material is generally characterized as approximately 50% by weight of polymer film sandwiched between two layers of paper tissue representing approximately the remaining 50% by weight of the laminate. The polymer is lightly cross-linked acrylic polymer as described in U.S. Pat. No. 4,117,184. Said laminate has a polymeric film weight ranging from about 32 to about 38 grams per square meter, a laminate weight in the range of about 62 to about 69 grams per square meter and a liquid capacity (polymer film portion without tissue) in the range of about 35 to 48 grams of 1% salt solution per gram of polymer film. For the best tissue material we recommend a 2 ply tissue or wadding weighing 39 grams per square meter and sold by Kimberly Clark under the grade designation K 40. For the sheath material it is presently preferred to employ Kendall Fiber Products Company Webline 146-039 NWF non-woven water permeable fabric formed of polyester filaments which weighs 21 grams per square meter.

While the relative amounts of polymeric layer material and tissue employed in the pad are not particularly critical, they should preferably be sufficient to meet the overall absorption capacity specifications set forth under "Summary of the Invention." At present it appears best to employ the method of FIGS. 16–40 to produce a pad with the undulating configuration illustrated in FIG. 29, using strips of raw material which are 31.8 centimeters wide to produce pads that are 25.4 centimeters long, the wrap and two-ply middle sheet being the aforementioned tissue and the two remaining sheets in the composite being the aforementioned Dow material.

One hundred fifteen 0.795 centimeter diameter substantially circular holes are punched in the composite in transverse rows with the centers of the holes in the respective rows being spaced apart approximately 2.5 centimeters both laterally and longitudinally, and with the number of holes in each row alternating between eleven and twelve. The holes in the eleven- and twelve-hole rows have their centers spaced, respectively, about 3.2 and 1.9 centimeters from the edges of the composite. These holes are of the hinge and flap configuration, corresponding in outline to the cutter of FIG. 18A, with the paper hinges being about 2 mm wide and having their sides cut at a radius of about 1 mm. Most of the flaps are folded back by about 90° or more from the adjoining portion of the composite and do not therefore block the holes. In this embodiment the total area of the two sheets of polymeric material in the composite is 1,615 cm$^2$, the area per opening is 0.496 cm$^2$, the combined total number of openings in the two hydrophilic sheets is 230, the total open area is 114.2 cm$^2$, the ratio of the total open area to total hydrophilic sheet area (without deduction for the open area) is 0.071 and the ratio of the total number of openings in the hydrophilic sheet material to the total area of the hydrophilic sheet material is 0.142.

The design just described is presently considered to have acceptable production characteristics, absorption rate and capacity and to be best on grounds of esthetics and comfort which are of course major factors in the consumer acceptability of products of this type.

Use of Pad in Incontinence Care

To easily insert pads into the briefs shown in FIGS. 1–4, a sitting position is recommended. In so doing, the briefs can be stretched between the legs, just above the knees, and the moisture-proof crotch panel 18 will then form a handy "work table." Insert the ends of the pad sheath extensions into the positioning loops 26,28 to hold the pad in place. For extra security the sheath extensions may be threaded around and through the loops a second time. The briefs may now be pulled up to give a snug fit; and the waist band can be positioned for comfort. Because the thermoplastic layer 22 of panel 18 faces to the interior of pants 10, absorption of urine or other liquids by the body 12 of the pants is minimized which helps to prevent embarrassing odors and stains. When the pad needs changing, the briefs can be lowered to the knees, and the pad removed from the positioning loops in any convenient position, such as while sitting on a toilet. By firmly grasping one of the sheath extensions and shaking, the pad can be caused to fall through the open end of the sheath into the toilet bowl water. When the sheath is formed of material which does not disintegrate in water, which is usually the case, it is placed in a waste receptacle rather than the toilet. Depending on the absorbent material used, it may be preferable to wait about 30 or more seconds before flushing to allow for partial disintegration of the used pad. In the meantime, a new pad can be inserted and one's clothing repositioned. The illustrated embodiment has been specifically designed to meet the needs of the ambulatory person (walking and sitting). For complete protection at night one can use the pads with conventional diapers.

Advantages

The pads and briefs described herein may be embodied in a wide variety of forms without departing from the spirit of the invention. Depending on the exact form or embodiment selected, one or more, or in some cases all, of the following advantages may be attained. The fact that one or several of the following advantages may not be attained, does not however demonstrate that a particular embodiment is not within the scope of the invention.

It is an advantage of the preferred embodiments of the pad that because of their combined high absorption rate and capacity per unit of volume and area, they need only cover the target area and can thus be quite compact. This leads to subsidiary advantages, such as ease in carrying or concealment, for example in the user's purse, freedom from bulkiness when worn, and ease in changing and disposal, without sacrificing protection. A light dry weight compared to liquid weight capacity is also an advantage. When the pad includes the above described hydrophilic paper, its dry weight versus liquid capacity ratio is quite strikingly low. Moreover, the gel formed by a hydrophilic paper when wetted resists loss of liquid under small amounts of compression; this, combined with the moisture proof panel in the brief, reduces the opportunity for wetting and staining of clothing and gives the wearer more comfort (perception of dryness) and confidence. Preferred embodiments of the pad are non-limiting, and offer reasonable cost versus liquid capacity. Moreover, the pads of the present embodiments do not make the tell-tale sound of rustling plastic associated with some other urinary incontinence care systems.

No special collection container is required for the pads, even when the hydrophilic paper is employed. The tissue paper readily disintegrates in water and the liquid gel and other components of the hydrophilic paper readily disperse on agitation and/or are biodegradeable in conventional sewage treatment processes. The hydrophilic paper is not harmful to the skin and in certain embodiments has a tendency to fix the nitrogen compounds which give urine its characteristic odor and potential for irritation of the skin.

When the pad is used with a sheath, as above described, and the sheath is preferably of hydrophobic material, it tends to produce a feeling of dryness against the skin even though the pad within may contain substantial amounts of moisture. When the ends of the sheath extend beyond the ends of the pad, they provide a dry area to grasp when changing the pad and disposing of it, such as into a storage container or toilet.

No special collection container is required for the sheath either. Although hydrophobic polymers such as polypropylene may resist biodegradation, their hydrophobicity and the amine-fixing capabilities of the hydrophilic paper cause the sheath to remain relatively dry and free of odor-forming materials. Thus, the used sheath may be disposed of in a conventional domestic or institutional waste container.

The use of briefs offers certain advantages in its own right. First and foremost, they are effective, providing secure confinement of liquid by holding one or more pads securely in the proper position. The crotch portion of the brief supports the pad and assists in retarding or barring transmission of liquid and/or odors.

The briefs are safe. They are manufactured of readily available materials which are not harmful to the skin, nor are they harmed by skin oils, moisture or urine, and they are comfortable when worn.

Use of the briefs is convenient. As illustrated above, they can be put on and taken off with an up-down motion familiar to users of menstrual pad and belt combinations. However, the briefs can be made in forms which open in the front or side, with convenient and quick fastening arrangements such as "Velcro" (trademark) hook and loop fabric, to facilitate putting on and taking off, as well as pad changing. Thus in most cases this urinary incontinence care device can be used without help from another person.

The briefs are also esthetically acceptable. Because of their light weight and especially their lack of bulkiness they can be readily hidden beneath clothes. Like the pads, they can be made of materials which are noiseless during walking and other body motions. They are readily cleansed and remain durable during repeated washings in household or institutional clothes washers and dryers.

Other advantages of the pads and briefs will be apparent to persons of ordinary skill in the art, moreover, it can readily be appreciated that the use of the preferred pad and preferred brief separately or in combination can provide unique combinations of advantages not heretofore available in known urinary incontinence care products.

We claim:

1. An absorbent pad having an absorptive layer including water-swellable material, said absorptive layer having openings for enhancing the rate of liquid absorbtion in said pad, and including hinge and flap members attached to the perimeters of said openings, said flap members extending away from said openings.

2. An absorbent pad as claimed in claim 1 which has opposed major surfaces, is of elongated shape and greater width than thickness, and wherein said water-swellable material is one which is capable of absorbing at least 35 times its own dry weight of water, said material constituting a sufficiently large proportion of the pad that its capacity for absorbing water constitutes at least about 50% that of the pad.

3. An absorbent pad as claimed in claim 2 wherein said absorptive layer is a composite having a plurality of layers including water-swellable material.

4. An absorbent pad as claimed in claim 2 wherein the absorptive capacity of said layer of water-swellable material for clear water is at least 60% of the total absorptive capacity of said absorbent pad for clear water.

5. An absorbent pad as claimed in claim 2 wherein said absorptive layer, as viewed in cross-section, has an undulating profile.

6. An absorbent pad as claimed in claim 5 wherein the undulating profile of said absorptive layer is formed by folds therein which alternate in opposite directions to form a plurality of panels of substantially varying or uniform width which are interspersed with said folds and which are arranged across the width of the pad, so that the edges of alternate folds are presented upwardly at or adjacent one of the major surfaces of the pad and the edges of intervening folds are presented downwardly at or adjacent the other of the major surfaces.

7. An absorbent pad as claimed in claim 2 wherein the openings are distributed throughout a substantial portion of the available surface of said absorptive layer, in such proportion that the ratio of the total open area of the openings to the total area of the portion (without deduction for the open area) is in the range of about 0.002 to about 0.25, wherein the open area per opening is in the range of about 0.02 to about 1.3 $cm^2$, and wherein there is from about 0.006 to about 0.3 opening per $cm^2$ of the area of that portion of the material in which the openings are distributed.

8. An absorbent pad as claimed in claim 2 wherein the openings are distributed throughout a substantial portion of the available surface of said absorptive layer, in such proportion that the ratio of the total open area of the openings to the total area of the portion (without deduction for the open area) is in the range of about 0.002 to about 0.2, wherein the open area per opening is in the range of about 0.05 to about 1 $cm^2$, and wherein there is from about 0.006 to about 0.25 opening per $cm^2$ of the area of that portion of the material in which the openings are distributed.

9. An absorbent pad as claimed in claim 1 which is of such size and wherein the identity and the quantity of the water-swellable material are such that the pad has a capacity of at least 200 cc natural or synthetic urine, and the pad is capable of absorbing at least 150 cc of natural or synthetic urine applied thereto at an evacuation or application rate of about 5 cc per second.

10. A brief with an absorbent pad as claimed in claim 1 therein.

11. A method for producing an absorbent pad, said method comprising the steps of making a plurality of cuts in an absorptive layer including a water-swellable material, each of said cuts forming a flap member which is attached to the absorptive layer by a hinge member, but is otherwise severed therefrom, and pushing the flap members away from the adjacent cuts, leaving openings with the flap members extending away therefrom.

12. A method as claimed in claim 11 which additionally includes the step of bringing two absorbent layers into juxtaposition with a tissue layer therebetween to form an absorptive layer, and wherein the steps of making a plurality of cuts and pushing the flap members are preformed on that absorptive layer.

13. A method as claimed in claim 11 which additionally includes the step of forming a plurality of undulations in the absorptive layer after the cuts have been made therein and the flap members have been pushed away from the adjacent cuts.

14. A method as claimed in claim 13 wherein the undulations are formed by making a plurality of folds in the absorptive layer which alternate in opposite directions to form a plurality of panels of substantially varying or uniform width which are interspersed with said folds and which are arranged across the width of the pad, so that the edges of alternate folds are presented upwardly at or adjacent one of the major surfaces of the pad and the edges of intervening folds are presented downwardly at or adjacent the other of the major surfaces.

15. A method as claimed in claim 11 wherein the cuts are made to provide openings which are distributed throughout a substantial portion of the available surface of the absorptive layer, in such proportion that the ratio of the total open area of the openings to the total area of the portion (without deduction for the open area) is in the range of about 0.002 to about 0.25, wherein the open area per opening is in the range of about 0.02 to about 1.3 $cm^2$, and wherein there is from about 0.006 to about 0.3 opening per $cm^2$ of the area of that portion of the material in which the openings are distributed.

16. A method as claimed in claim 11 wherein the cuts, in plan view, extend in one direction in an arc from one side of the adjacent hinge members to the opposed side thereof, and, in the opposite direction, diverge from one another to inhibit tear propagation in the absorptive layer adjacent the hinge members.

17. A method as claimed in claim 12 wherein the cuts, in plan view, extend in one direction in an arc from one side of the adjacent hinge members to the opposed side thereof, and, in the opposite direction, diverge from one another to inhibit tear propagation in the absorptive layer adjacent the hinge members.

18. A method as claimed in claim 13 wherein the cuts, in plan view, extend in one direction in an arc from one side of the adjacent hinge members to the opposed side thereof, and, in the opposite direction, diverge from one another to inhibit tear propagation in the absorptive layer adjacent the hinge members.

19. A method as claimed in claim 14 wherein the cuts, in plan view, extend in one direction in an arc from one side of the adjacent hinge members to the opposed side thereof, and, in the opposite direction, diverge from one another to inhibit tear propagation in the absorptive layer adjacent the hinge members.

20. A method as claimed in claim 15 wherein the cuts, in plan view, extend in one direction in an arc from one side of the adjacent hinge members to the opposed side thereof, and, in the opposite direction, diverge from one another to inhibit tear propagation in the absorptive layer adjacent the hinge members.

21. An absorbent pad as claimed in claim 1 which additionally includes a water-insoluble outer sheath which encloses said absorptive layer on at least four sides, said sheath having an opening through which said absorptive layer can be discharged from said sheath after use for separate disposal.

22. An absorbent pad as claimed in claim 1 which additionally includes a water-insoluble outer sheath which encloses said absorptive layer on at least four sides, said sheath having an openable region in which it can be opened after use of the pad to provide an opening through which said absorptive layer can be discharged from said sheath for separate disposal.

* * * * *